(12) United States Patent
Ameer

(10) Patent No.: US 11,850,328 B2
(45) Date of Patent: Dec. 26, 2023

(54) BODY TEMPERATURE-TRIGGERED, IN SITU FORMING BIOMATERIALS AND DEVICES

(71) Applicant: Northwestern University, Evanston, IL (US)

(72) Inventor: Guillermo A. Ameer, Chicago, IL (US)

(73) Assignee: Northwestern University, Evanston, IL (US)

(*) Notice: Subject to any disclaimer, the term of this patent is extended or adjusted under 35 U.S.C. 154(b) by 243 days.

(21) Appl. No.: 16/349,186

(22) PCT Filed: Nov. 14, 2017

(86) PCT No.: PCT/US2017/061582
§ 371 (c)(1),
(2) Date: May 10, 2019

(87) PCT Pub. No.: WO2018/090021
PCT Pub. Date: May 17, 2018

(65) Prior Publication Data
US 2019/0282735 A1    Sep. 19, 2019

Related U.S. Application Data

(60) Provisional application No. 62/421,753, filed on Nov. 14, 2016.

(51) Int. Cl.
| | |
|---|---|
| *A61L 27/46* | (2006.01) |
| *A61K 9/00* | (2006.01) |
| *A61K 9/08* | (2006.01) |
| *A61K 47/32* | (2006.01) |
| *A61L 27/18* | (2006.01) |
| *A61L 27/50* | (2006.01) |
| *C08G 63/47* | (2006.01) |
| *C08G 63/91* | (2006.01) |
| *C08L 67/00* | (2006.01) |
| *C08L 101/00* | (2006.01) |
| *A61L 27/16* | (2006.01) |
| *C08L 101/16* | (2006.01) |

(52) U.S. Cl.
CPC .......... *A61L 27/46* (2013.01); *A61K 9/00* (2013.01); *A61K 9/0024* (2013.01); *A61K 47/32* (2013.01); *A61L 27/16* (2013.01); *A61L 27/18* (2013.01); *A61L 27/50* (2013.01); *C08G 63/47* (2013.01); *C08G 63/914* (2013.01); *C08L 67/00* (2013.01); *C08L 101/00* (2013.01); *C08L 101/16* (2013.01); *A61L 2300/802* (2013.01); *A61L 2430/02* (2013.01)

(58) Field of Classification Search
CPC ...... C08L 33/04; C08L 67/00; C08L 1010/00; C08L 101/16; A61L 27/32; A61L 27/10; A61L 27/12; A61L 27/46; A61L 27/16; A61L 27/18; A61L 27/50; A61L 2300/802; A61L 2430/02; A61K 9/0024; A61K 9/08; A61K 47/32; C08G 63/47; C08G 63/914

See application file for complete search history.

(56) References Cited

U.S. PATENT DOCUMENTS

| | | | |
|---|---|---|---|
| 5,891,960 A | 4/1999 | Claar et al. | |
| 8,404,264 B2 | 3/2013 | Ameer et al. | |
| 8,568,765 B2 | 10/2013 | Ameer et al. | |
| 8,580,912 B2 | 11/2013 | Ameer et al. | |
| 8,758,796 B2 | 6/2014 | Ameer et al. | |
| 8,772,437 B2 | 7/2014 | Ameer et al. | |
| 8,911,720 B2 | 12/2014 | Ameer et al. | |
| 8,912,248 B2 * | 12/2014 | Shimohara | C09B 69/101 523/160 |
| 10,463,745 B2 | 11/2019 | Zhu et al. | |
| 2003/0118692 A1 | 6/2003 | Wang et al. | |
| 2013/0211500 A1 | 8/2013 | Kibbe et al. | |
| 2014/0037588 A1 | 2/2014 | Yang et al. | |
| 2014/0058049 A1 | 2/2014 | Ameer et al. | |
| 2014/0135407 A1 | 5/2014 | Ameer et al. | |
| 2014/0155516 A1 | 6/2014 | Ameer et al. | |
| 2014/0350187 A1 * | 11/2014 | Ito | C08J 5/18 525/190 |

FOREIGN PATENT DOCUMENTS

| | | | | |
|---|---|---|---|---|
| WO | WO-2014131375 A2 * | 9/2014 | ........... | A61L 27/446 |
| WO | WO-2016176444 A1 * | 11/2016 | ............... | A61F 2/82 |

OTHER PUBLICATIONS

Zhao et al. (Journal of Applied Polymer Science (2009), vol. 114, p. 1464-1470). (Year: 2009).*
Fonseca et al., Synthesis of unsaturated polyesters based on renewable monomers: Structure/properties relationship and crosslinking with 2-hydroxyethyl methacrylate, Reactive and Functional Polymers, 97, pp. 1-11. Available online Oct. 8, 2015. (Year: 2015).*
Franklin, David S., and Selvam Guhanathan. "Influence of chain length of diol on the swelling behavior of citric acid based pH sensitive polymeric hydrogels: A green approach." Journal of Applied Polymer Science 132.5 (2015). (Year: 2015).*
Reis, Adriano V., et al. "Reaction of glycidyl methacrylate at the hydroxyl and carboxylic groups of poly (vinyl alcohol) and poly (acrylic acid): is this reaction mechanism still unclear?." The Journal of organic chemistry 74.10 (2009): 3750-3757. (Year: 2009).*

(Continued)

*Primary Examiner* — Abigail Vanhorn
(74) *Attorney, Agent, or Firm* — Casimir Jones, S.C.; David W. Staple

(57) ABSTRACT

Provided herein are thermoresponsive polymer materials and methods of preparation and use thereof. In particular, materials are provided that cure upon exposure to physiologic conditions (e.g., human body temperature) and find use in, for example, orthopedic surgery, bone tissue engineering, and the repair of bone injuries and defects.

11 Claims, 32 Drawing Sheets

(56) References Cited

OTHER PUBLICATIONS

Amini et al., Bone tissue engineering: recent advances and challenges. Crit Rev Biomed Eng. 2012;40(5):363-408.

Arshady, Preparation of biodegradable microspheres and microcapsules: 2. Polyactides and related polyesters. J. Controlled Release 17:1-22, 1991.

Chia et al., Radiation curing of poly-methyl-methacrylate using a variable power microwave source. J Mater Processing Tech. 1995;48(1-4):445-449.

Chien et al., High viability of cells encapsulated in degradable poly(carboxybetaine) hydrogels. Langmuir. 2012;28(51):17778-17784.

Chon et al., Synthesis of a high-performance citric acid-based polyester elastomer by a hot-pressing technique. Polymer 2017;125:283-291.

Dae Han et al., Analysis of the curing behavior of unsaturated polyester resins using the approach of free radical polymerization. J Appl. Polym. Sci. 1987;33:2859-2876.

Daldy et al., Increasing hydroxyapatite incorporation into poly(methyl methacrylate) cement increases osteoblast adhesion and response. Biomaterials. 2002;23(2):569-576.

Gosain et al., A 1-year study of os-teoinduction in hydroxyapatite-derived biomaterials in an adult sheep model: part I. Plast Reconstr Surg. 2002;109(2):619-630.

Hasegawa et al., In vivo evaluation of a porous hydroxyapatite/poly-DL-lactide composite for bone tissue engineering. J Biomed Mater Res A. 2007;81(4):930-938.

Higashi et al., Polymer-hydroxyapatite composites for biodegradable bone fillers. Biomaterials. 1986;7(3):183-187.

Holland et al., Polymers for biodegradable medical devices. 1. The potential of polyesters as controlled macromolecular release systems. J. Controlled Release 1986;4:155-0180.

Kühn K-D. Properties of bone cement: what is bone cement. In: Breusch S, Malchau H, eds. The well cemented total hip arthroplasty. Heidelberg: Springer Medizin Verlag, 2005:52-9.

Morgan et al., Mechanical properties of carbonated apatite bone mineral substitute: strength, fracture, and fatigue behavior. J. Mater. Sci. Mater. Med. 1997;8:559-570.

Peniche et al., Self-curing membranes of chitosan/PAA IPNs obtained by radical polymerization: preparation, characterization, and interpolymer complexation. Biomaterials. 1999;20(10):1869-1878.

Peter et al., In vivo degradation of poly(propylene fumarate)/beta-tricalcium phosphate injectable composite scaffold. J Biomed Mater Res. 1998;41:1-7.

Pitt, The controlled parenteral delivery of polypeptides and proteins. Int. J. Pharm. 59:173-196, 1990.

Rezwan et al., Biodegradable and bioactive porous polymer/inorganic composite scaffolds for bone tissue engineering. Biomaterials. Jun. 2006;27(18):3413-31.

Stephenson et al., The effect of hydroxyapatite coating on ingrowth of bone into cavities of an implant. J Arthroplasty. 1991;6:51-58.

Storey et al., Methacrylate-endcapped poly(d,l-lactide-co-trimethylene carbonate) oligomers. Network formation by thermal free-radical curing. Polymer 1997;38(26):6295-6301.

Wako Pure Chemical Industries, Azo Polymerization Initiators Comprehesive Catalog. Apr. 22, 2006. 36 pages.

Wang et al. Photo-crosslinked Biodegradable Elastomers for Controlled Nitric Oxide Delivery. (Biomater Sci. Jun. 2013;1(6):625-632.

Webb et al., Biodegradable polyester elastomers in tissue engineering. Expert Opin Biol Ther 2004;4:801-12.

Webb et al., The role of polymethylmethacrylate bone cement in modern orthopaedic surgery. J Bone Joint Surg. 2007;89-B:851-7.

Yang et al., Novel citric acid-based biodegradable elastomers for tissue engineering. Adv Mater 2004;16:511-6.

Yang et al., Synthesis and evaluation of poly(diol citrate) biodegradable elastomers. Biomaterials, 2006. 27(9):1889-98.

Zhao et al., Modulating the Mechanical Properties of Poly(diol citrates) via the Incorporation of a Second Type of Crosslink Network. J Appl PolymerScience 2009;114:1464-70.

International Search Report and Written Opinion for PCT/US2017/061582, dated Jan. 29, 2018, 13 pages.

\* cited by examiner

| | Specimen label | Diameter (mm) | Anvil height (mm) | Modulus (MPa) |
|---|---|---|---|---|
| | 1 | 9.00000 | 5.00000 | 2.71811 |
| | 2 | 9.00000 | 5.00000 | 2.47170 |
| | 3 | 9.00000 | 5.00000 | 2.11800 |
| | 4 | 9.00000 | 5.00000 | 3.58165 |
| Mean | | 9.00000 | 5.00000 | 2.72236 |
| Standard Deviation | | 0.00000 | 0.00000 | 0.62356 |
| Maximum | | 9.00000 | 5.00000 | 3.58165 |
| Minimum | | 9.00000 | 5.00000 | 2.11800 |

|   | Specimen label | Diameter (mm) | Anvil height (mm) | Modulus (MPa) |
|---|---|---|---|---|
|   | 1 | 9.00000 | 5.00000 | 9.50162 |
|   | 2 | 9.00000 | 5.00000 | 6.72120 |
|   | 3 | 9.00000 | 5.00000 | 8.17287 |
|   | 4 | 9.00000 | 5.00000 | 10.63902 |
| Mean |   | 9.00000 | 5.00000 | 8.75868 |
| Standard Deviation |   | 0.00000 | 0.00000 | 1.69136 |
| Maximum |   | 9.00000 | 5.00000 | 10.63902 |
| Minimum |   | 9.00000 | 5.00000 | 6.72120 |

| | Specimen label | Diameter (mm) | Anvil height (mm) | Modulus (MPa) |
|---|---|---|---|---|
| | 1 | 9.00000 | 5.00000 | 1.47191 |
| | 2 | 9.00000 | 5.00000 | 2.16377 |
| | 3 | 9.00000 | 5.00000 | 1.37996 |
| | 4 | 9.00000 | 5.00000 | 2.27322 |
| Mean | | 9.00000 | 5.00000 | 1.82222 |
| Standard Deviation | | 0.00000 | 0.00000 | 0.46129 |
| Maximum | | 9.00000 | 5.00000 | 2.27322 |
| Minimum | | 9.00000 | 5.00000 | 1.37996 |

| | Specimen label | Diameter (mm) | Anvil height (mm) | Modulus (MPa) |
|---|---|---|---|---|
| | 1 | 9.00000 | 5.00000 | 27.79747 |
| | 2 | 9.00000 | 5.00000 | 30.32288 |
| | 3 | 9.00000 | 5.00000 | 22.50099 |
| | 4 | 9.00000 | 5.00000 | 28.88112 |
| Mean | | 9.00000 | 5.00000 | 27.37561 |
| Standard Deviation | | 0.00000 | 0.00000 | 3.41042 |
| Maximum | | 9.00000 | 5.00000 | 30.32288 |
| Minimum | | 9.00000 | 5.00000 | 22.50099 |

|  | Specimen label | Diameter (mm) | Anvil height (mm) | Modulus (MPa) |
|---|---|---|---|---|
|  | 1 | 9.00000 | 5.00000 | 1.44970 |
|  | 2 | 9.00000 | 5.00000 | 1.58808 |
| Mean |  | 9.00000 | 5.00000 | 1.51889 |
| Standard Deviation |  | 0.00000 | 0.00000 | 0.09785 |
| Maximum |  | 9.00000 | 5.00000 | 1.58808 |
| Minimum |  | 9.00000 | 5.00000 | 1.44970 | mPDC mPDC-40HA mPOC

_BODY TEMPERATURE-TRIGGERED, IN SITU FORMING BIOMATERIALS AND DEVICES_

CROSS REFERENCE TO RELATED APPLICATIONS

The present application claims the priority benefit of U.S. Provisional Patent Application No. 62/421,753, filed Nov. 14, 2016, which is incorporated by reference in its entirety.

FIELD

Provided herein are thermoresponsive polymer materials and methods of preparation and use thereof. In particular, materials are provided that cure upon exposure to physiologic conditions (e.g., human body temperature) and find use in, for example, orthopedic surgery, bone tissue engineering, and the repair of bone injuries and defects.

BACKGROUND

Currently, reconstructive and orthopedic surgeons do not have a suitable arsenal of safe and effective materials to repair bone injuries, stabilize complex fractures, or implant fixation devices in a manner that promotes the rapid regeneration of healthy bone.

SUMMARY

Provided herein are thermoresponsive polymer materials and methods of preparation and use thereof. In particular, materials are provided that cure upon exposure to physiologic conditions (e.g., human body temperature) and find use in, for example, orthopedic surgery, bone tissue engineering, and the repair of bone injuries and defects.

In some embodiments, provided herein are compositions comprising an acrylated or methacrylated polymer and a thermoresponsive initiator compound, wherein an increase in temperature above a threshold temperature results in radical formation from the thermoresponsive initiator compound, and the radical formation initiates curing of the acrylated or methacrylated polymer into a cured polymer. In some embodiments, the acrylated or methacrylated polymer is a liquid and/or is soluble in water and/or organic solvent. In some embodiments, the cured polymer is a solid and/or is insoluble in water and/or organic solvent. In some embodiments, the acrylated or methacrylated polymer is a biodegradable and/or biocompatible polyester. In some embodiments, the acrylated or methacrylated polymer is a citric acid-based polyester. In some embodiments, the citric acid-based polyester comprises citric acid and linear aliphatic diol monomers. In some embodiments, the citric acid-based polyester comprises a poly(diol citrate). In some embodiments, the diol is a linear aliphatic diol, X carbons in length, wherein X is between 2 and 20, and comprising OH groups on the 1 and X carbons. In some embodiments, the diol is selected from the group consisting of 1,4-butanediol, 1,6-hexanediol, 1,8-octanediol, 1,10-decanediol, 1,12-dodecanediol, 1,14-quattuordecanediol, and 1,16-sedecimanediol. In some embodiments, at least 10% (e.g., 10%, 25%, 30%, 35%, 40%, 45%, 50%, 55%, 60%, 65%, 70%, 75%, 80%, 85%, 90%, or ranges therebetween) of the citric acid monomers of the acrylated or methacrylated polymer display a methacrylate or acrylate. In some embodiments, the thermoresponsive initiator compound is a diazo compound. In some embodiments, the thermoresponsive initiator compound is selected from the group consisting of 65, V-70, V-40, V-50, V-59, VA-044, VA-057, VA-061, VA-086, and BPO.

In some embodiments, provided herein are compositions comprising a cured polymer composition prepared by the thermally-induced curing of a composition comprising an acrylated or methacrylated polymer and a thermoresponsive initiator compound, as described herein. In some embodiments, thermally-induced curing occurs at a temperature between 32 and 43° C. (e.g., 32° C., 33° C., 34° C., 35° C., 36° C., 37° C., 38° C., 39° C., 40° C., 41° C., 42° C., 43° C., or ranges therebetween). In some embodiments, curing (e.g., liquid to solid phase change) occurs in less than 30 minutes (e.g., 1 minute, 2 minutes, 5 minutes, 10 minutes, 15 minutes, 20 minutes, 25 minutes, 30 minutes, or ranges therebetween) once the composition is at the inducing temperature.

In some embodiments, provided herein are composite materials comprising (a) a composition comprising an acrylated or methacrylated polymer and a thermoresponsive initiator compound, as described herein; and (b) one or more additional structural components. In some embodiments, the additional structural components comprise at least 10 wt % (e.g., 10%, 25%, 30%, 35%, 40%, 45%, 50%, 55%, 60%, 65%, 70%, 75%, 80%, 85%, 90%, or ranges therebetween) of the composite material. In some embodiments, the one or more additional structural components comprises a biodegradable and/or biocompatible polymer. In some embodiments, the one or more additional structural components comprises a bioceramic. In some embodiments, the bioceramic comprises hydroxyapatite (HA) and/or tricalcium phosphate beta (β TCP).

In some embodiments, provided herein are compositions comprising a cured composite material prepared by the thermally-induced curing of a composite material comprising (a) a composition comprising an acrylated or methacrylated polymer and a thermoresponsive initiator compound, as described herein; and (b) one or more additional structural components, as described herein.

In some embodiments, provided herein are compositions comprising an acrylated or methacrylated poly(diol citrate) polymer and a thermoresponsive diazo initiator compound, wherein an increase in temperature above a threshold temperature results in radical formation from the thermoresponsive diazo initiator compound, and the radical formation initiates curing of the acrylated or methacrylated poly(diol citrate) polymer into a cured poly(diol citrate) polymer, wherein the acrylated or methacrylated polymer is a liquid and the cured polymer is a solid.

In some embodiments, provided herein are methods comprising administering a composition comprising an acrylated or methacrylated poly(diol citrate) polymer and a thermoresponsive diazo initiator compound, as described herein, to a bone defect or fracture and allowing the composition to cure.

In some embodiments, provided herein is the use of a comprising an acrylated or methacrylated poly(diol citrate) polymer and a thermoresponsive diazo initiator compound, as described herein, to repair a bone defect or fracture.

BRIEF DESCRIPTION OF THE DRAWINGS

(FIGS. 1A, C) $^1$H-NMR spectrum of mPOC and mPDC, respectively. The presence of the peaks labeled A through E-2 in the spectrum confirms the successful functionalization of POC and PDDC with the methacrylate group. The peaks labeled F correspond to the methylene protons from citric acid, and peaks G through J and L were assigned to protons from 1,8-dodecanediol and 1,12-dodecanediol, respectively. (FIGS. 1B, D) FTIR spectrum of POC and mPOC. The presence of the peak at 1600 cm$^{-1}$ for mPOC and mPDC corresponds to the methacrylate alkene, confirming the successful methacrylation of POC and PDDC.

(FIG. 2A) mPOC. (FIG. 2B) mPDC. (FIG. 2C) mPOC-20HA. (FIG. 2D) mPDC-20HA. (FIG. 2E) mPOC-40HA. (FIG. 2F) mPDC-40HA. The data represents two independent experiments for each formulation group.

(FIG. 3A) mPOC. (FIG. 3B) mPDC. (FIG. 3C) mPOC-20HA. (FIG. 3D) mPOC-40HA. (FIG. 3E) mPDC-40HA. The compression tests were performed in accordance with the ASTM F451 standard. The polymer only group exhibited higher ultimate compressive strength and modulus compared to the composites. The data represents five independent experiments for each formulation group.

FIG. 9A-B. Graphs depicting material temperature during curing in the presence of V70 initiator, without accelerator, for (a) mPOC and (B) mPDC-40HA.

DEFINITIONS

Figure 1A:
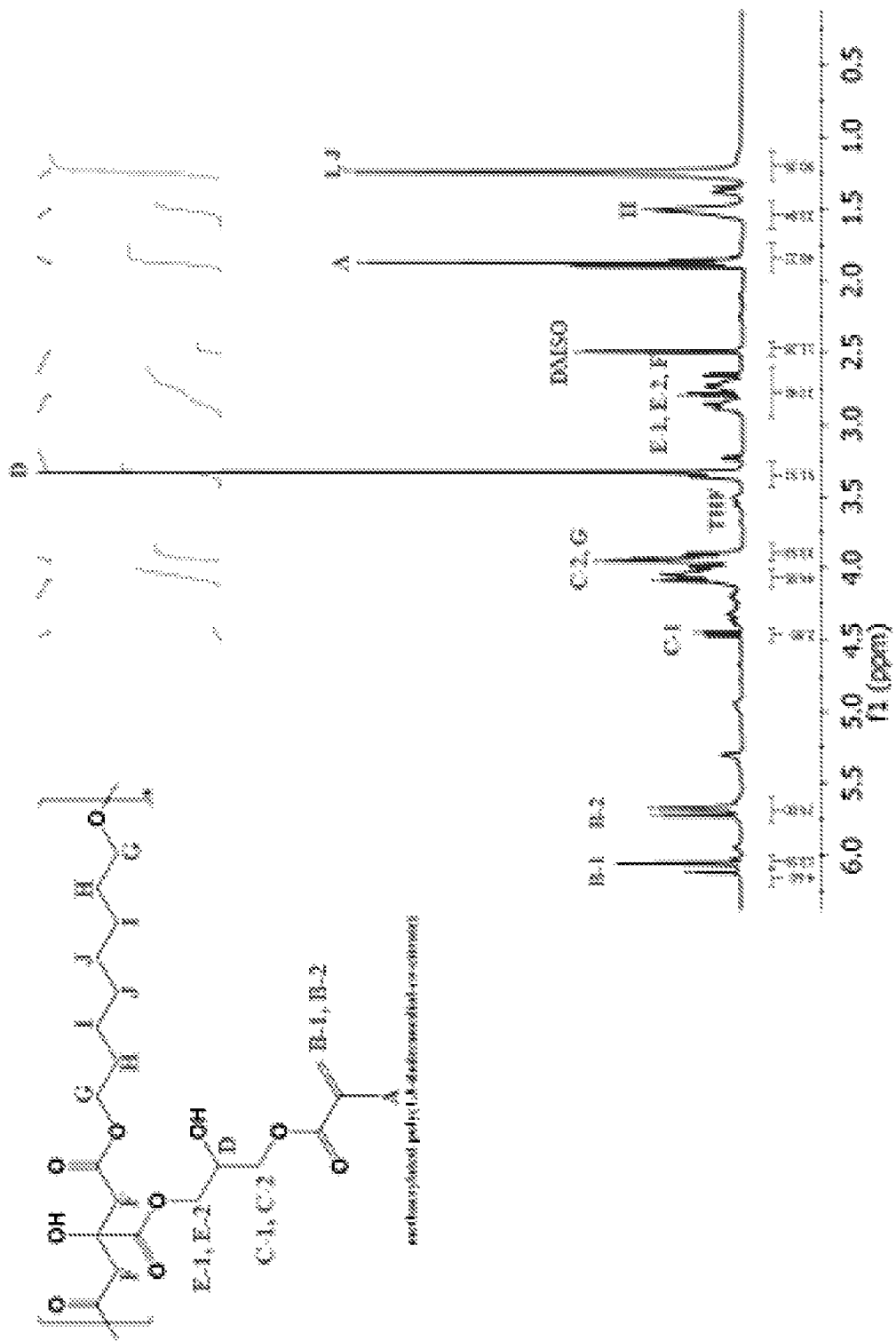
FIGS. 1A-D. Chemical characterization methacrylated poly(diol citrate).
Figure 1B:
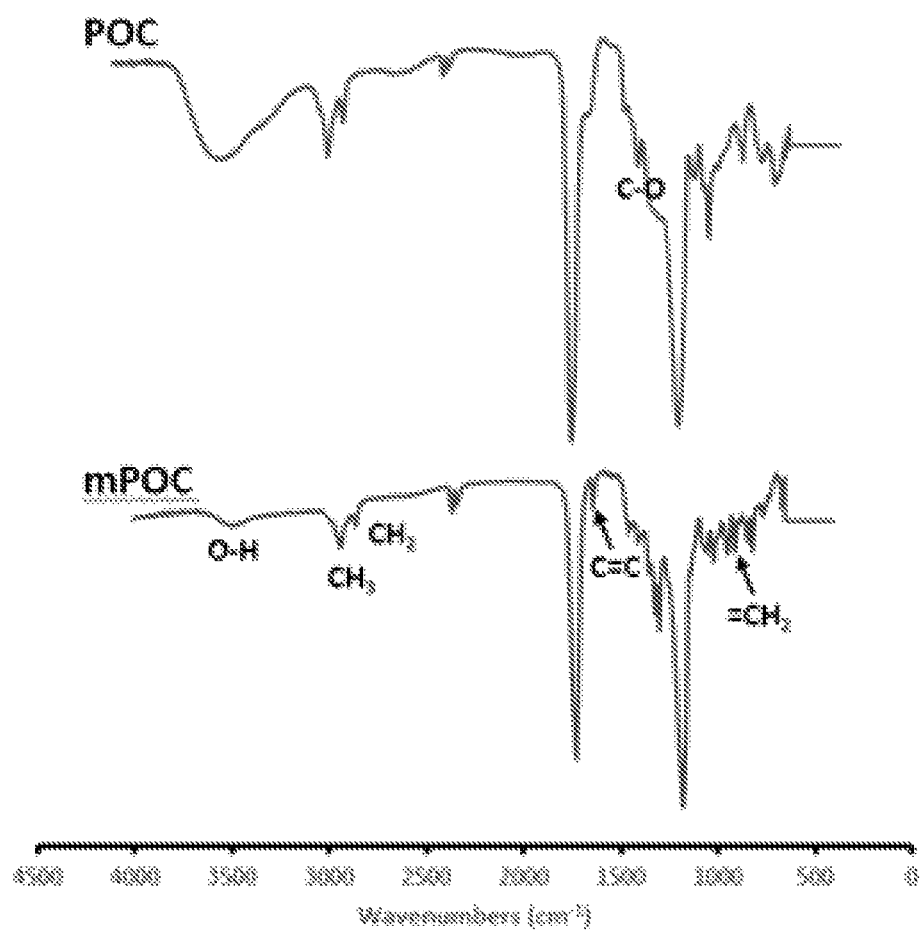
Figure 1C:
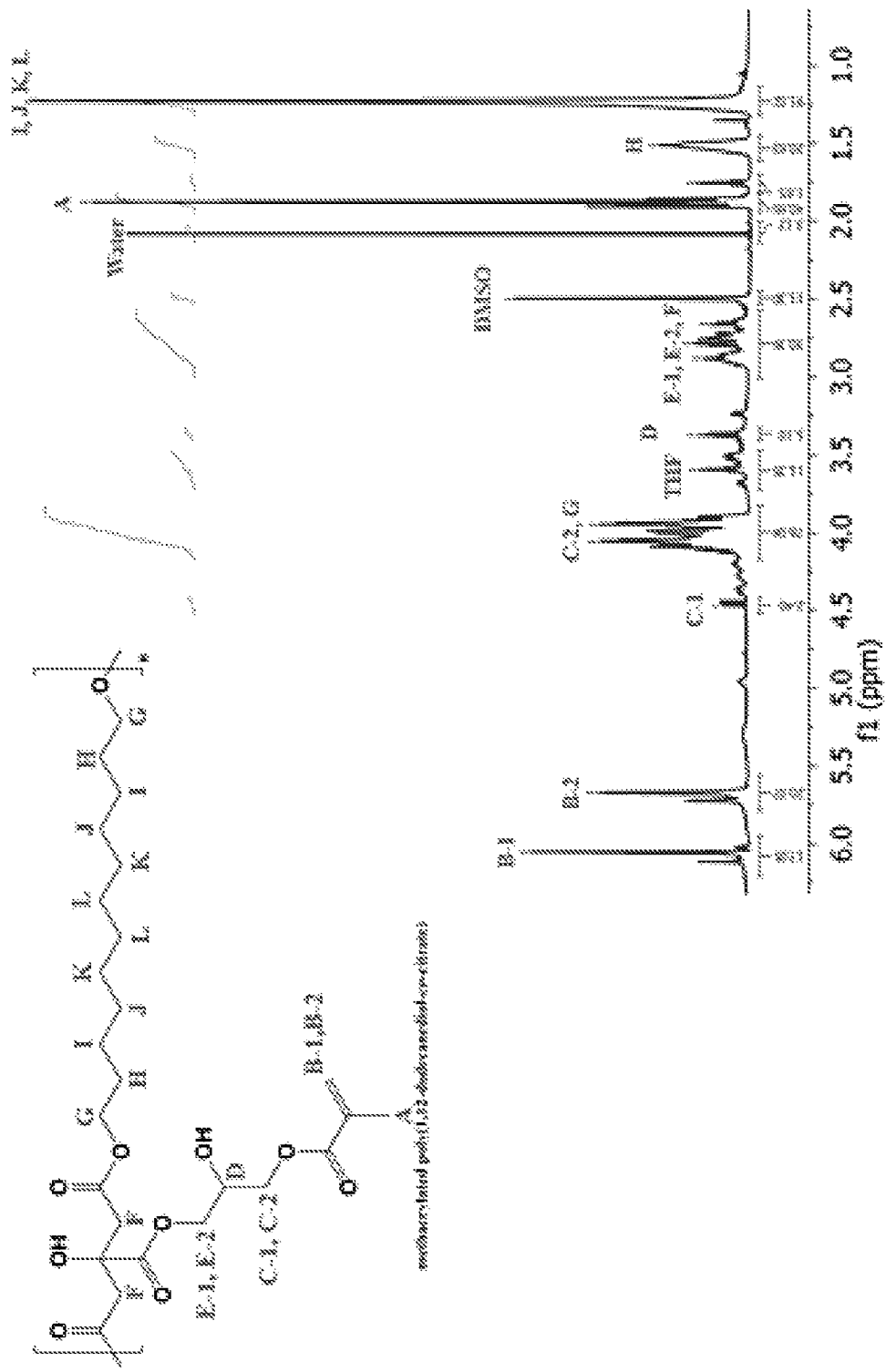
Figure 1D:
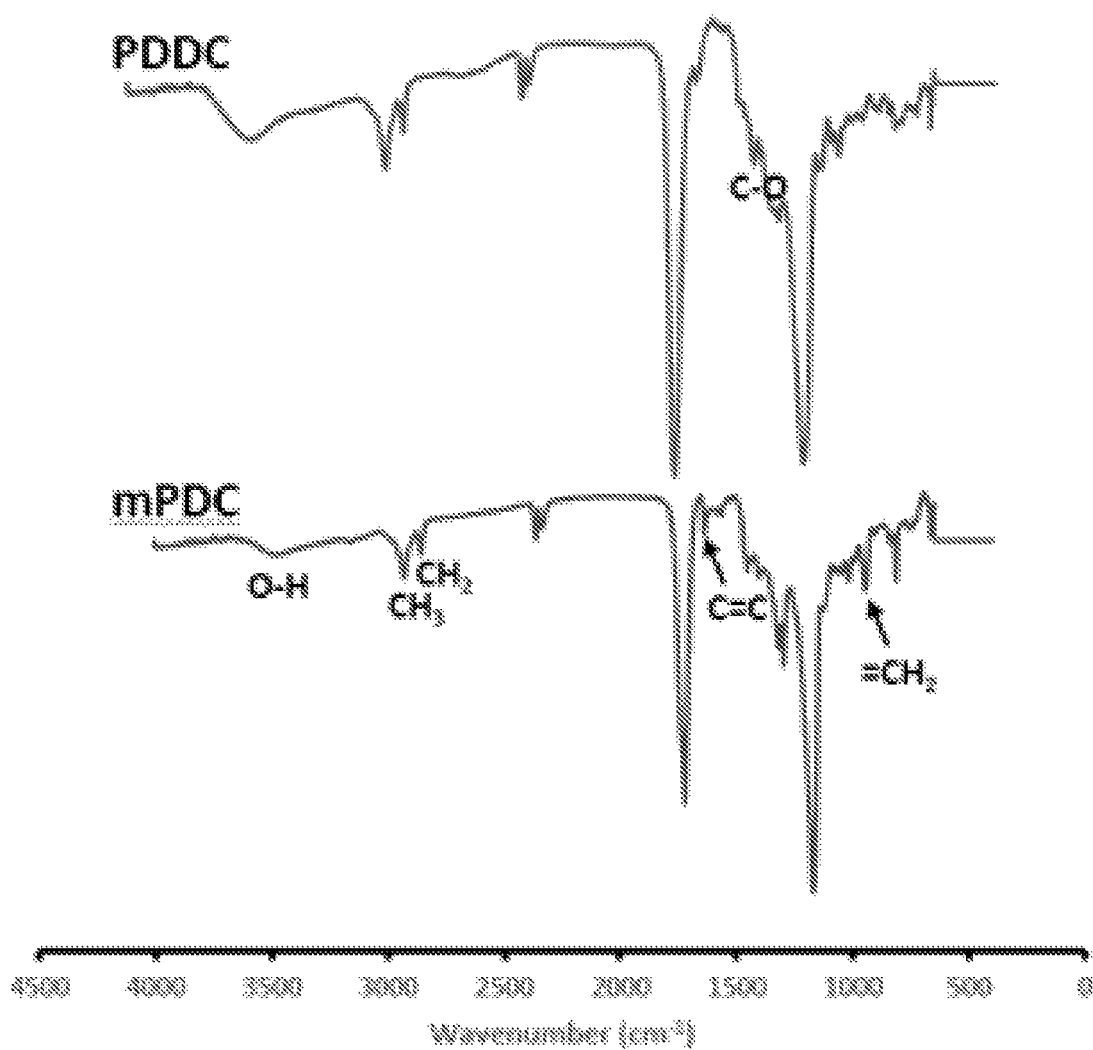
Figure 2A:
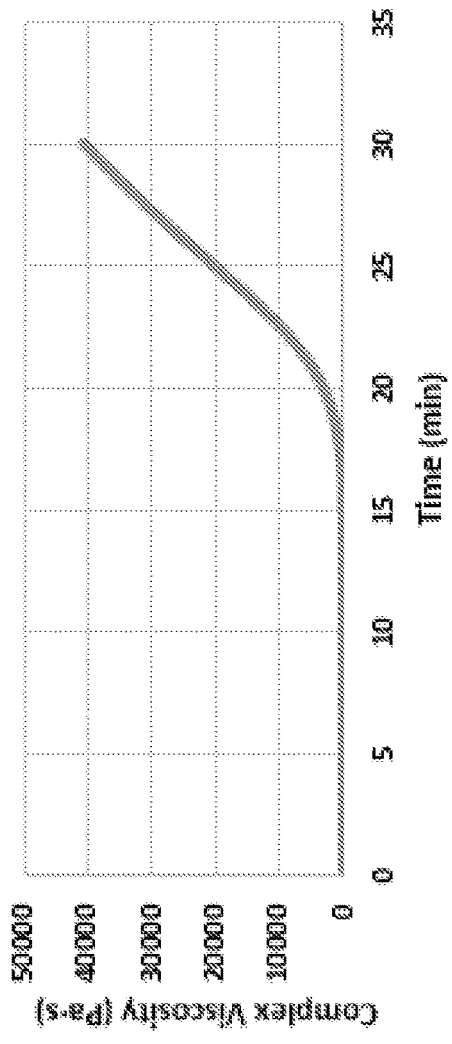
FIGS. 2A-F. Quantitative gel point measurement with rheology.
Figure 2B:
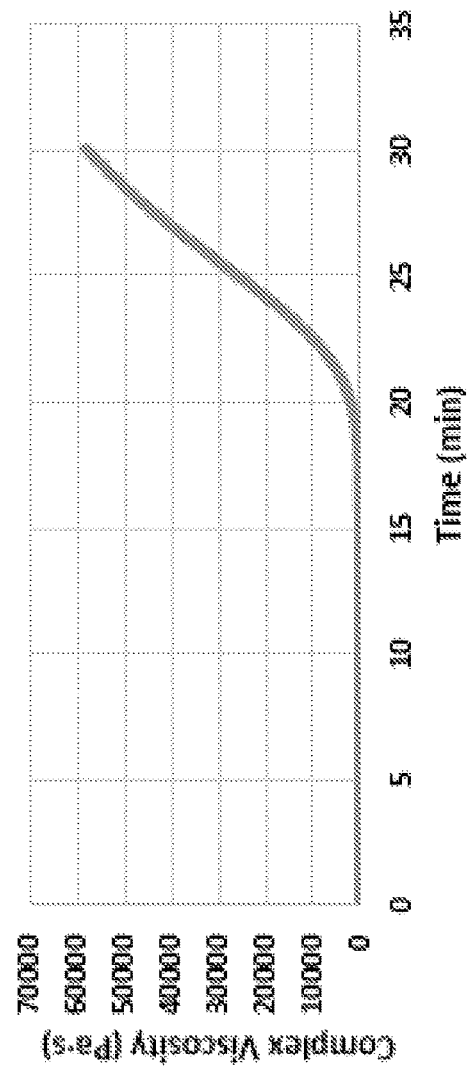
Figure 2C:
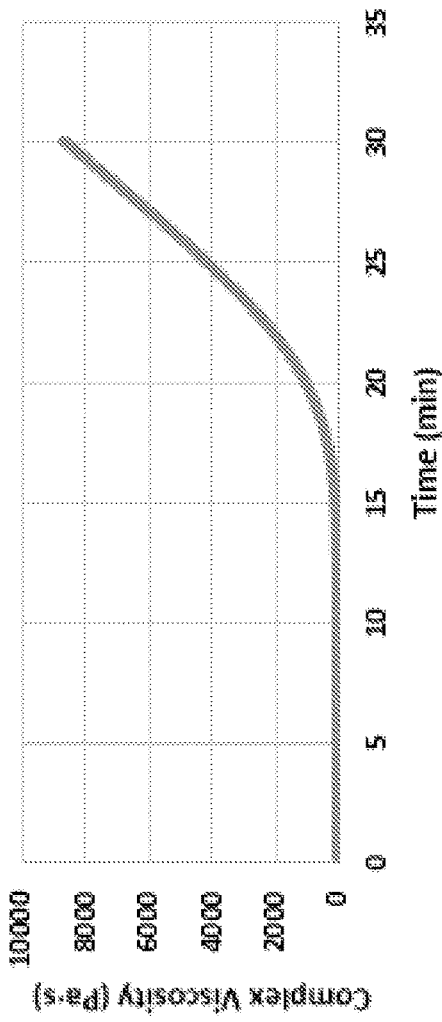
Figure 2D:
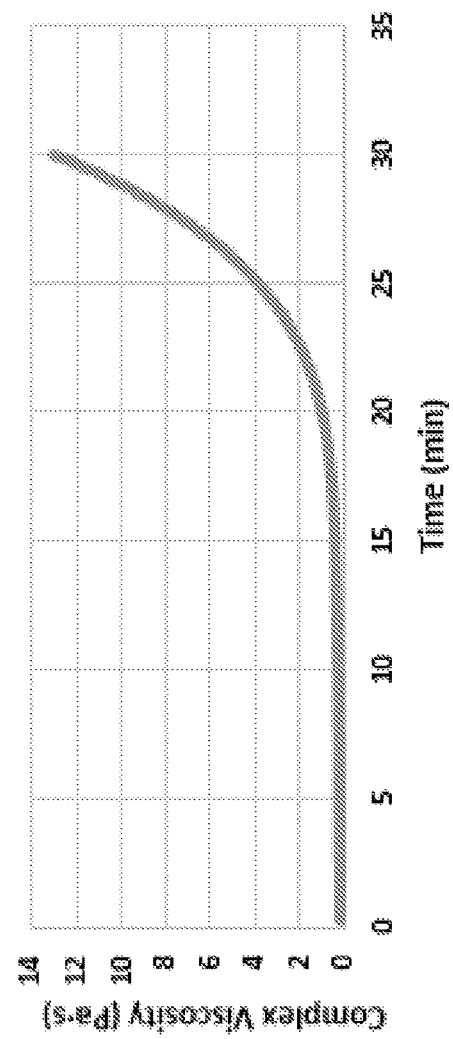
Figure 2E:
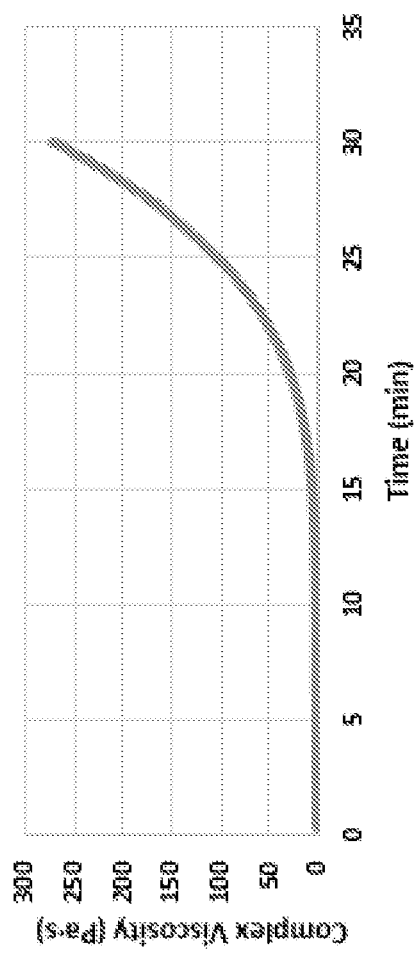
Figure 2F:
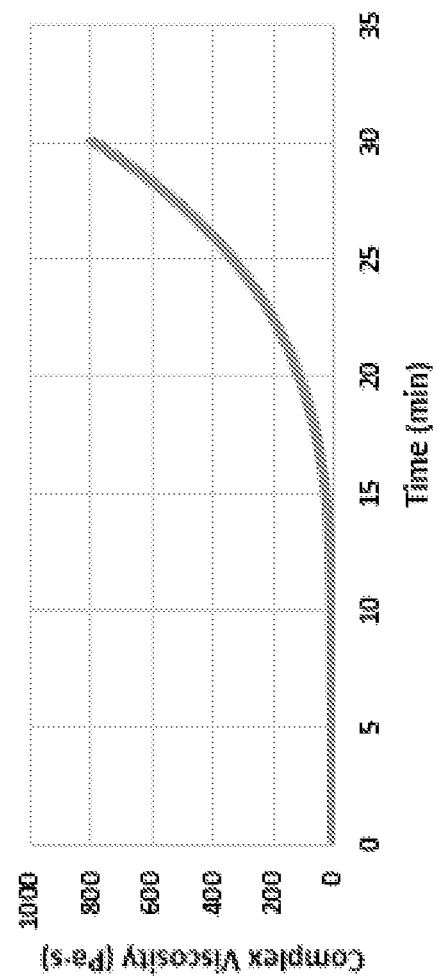
Figure 3A:
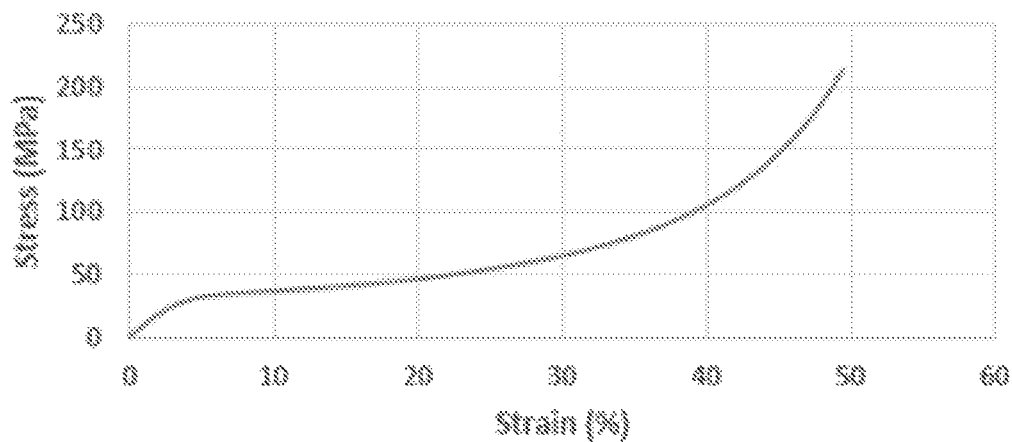
FIGS. 3A-E. Stress-strain curve for tested formulations.
Figure 3B:
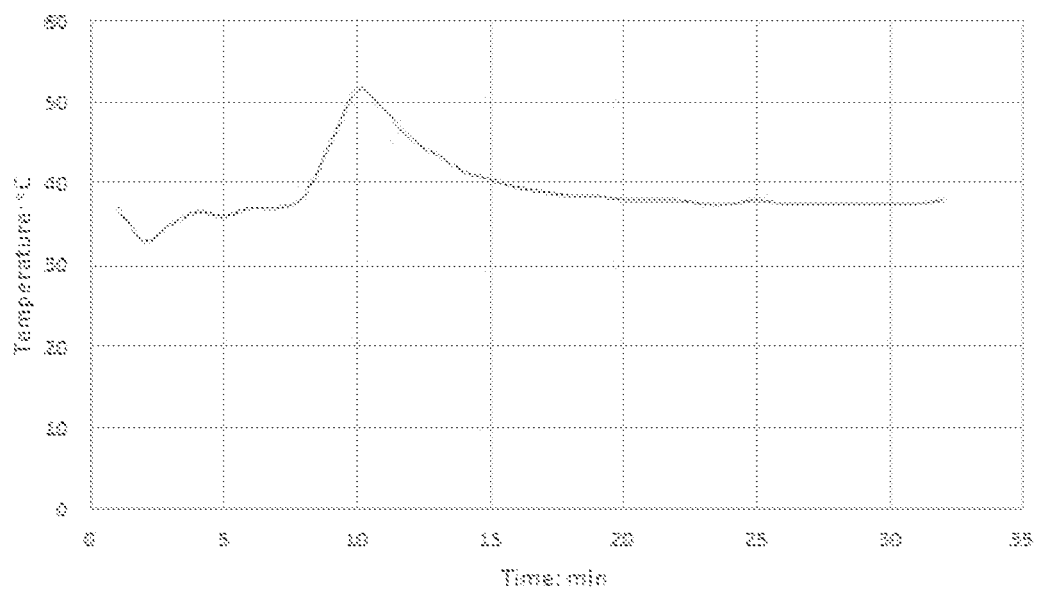
Figure 3C:
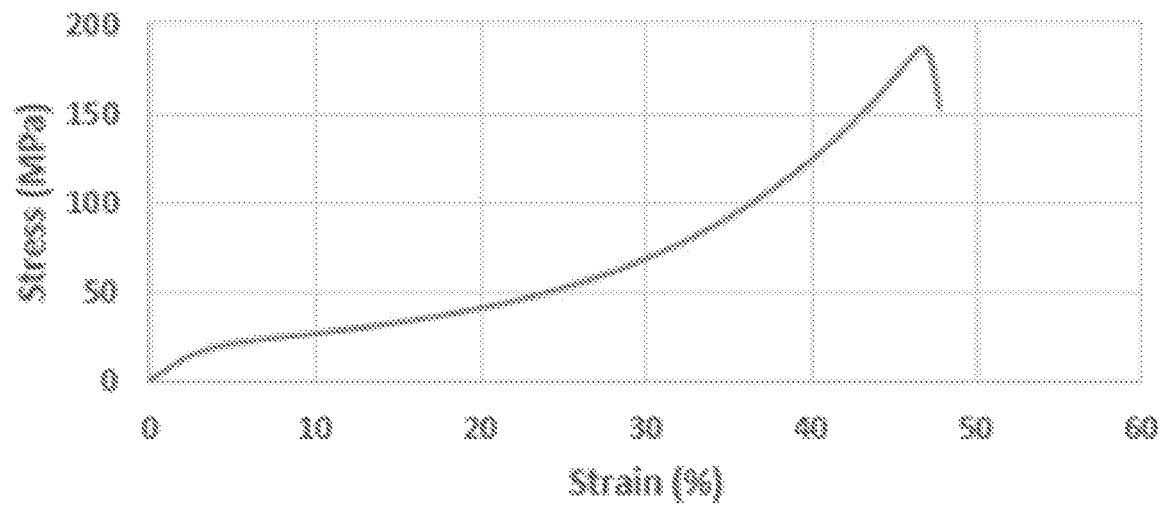
Figure 3D:
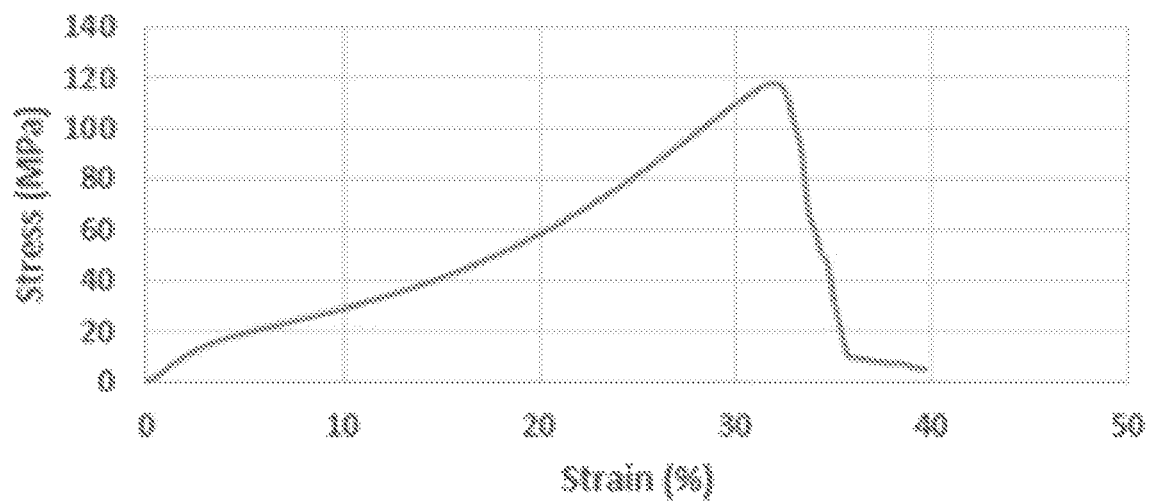
Figure 3E:
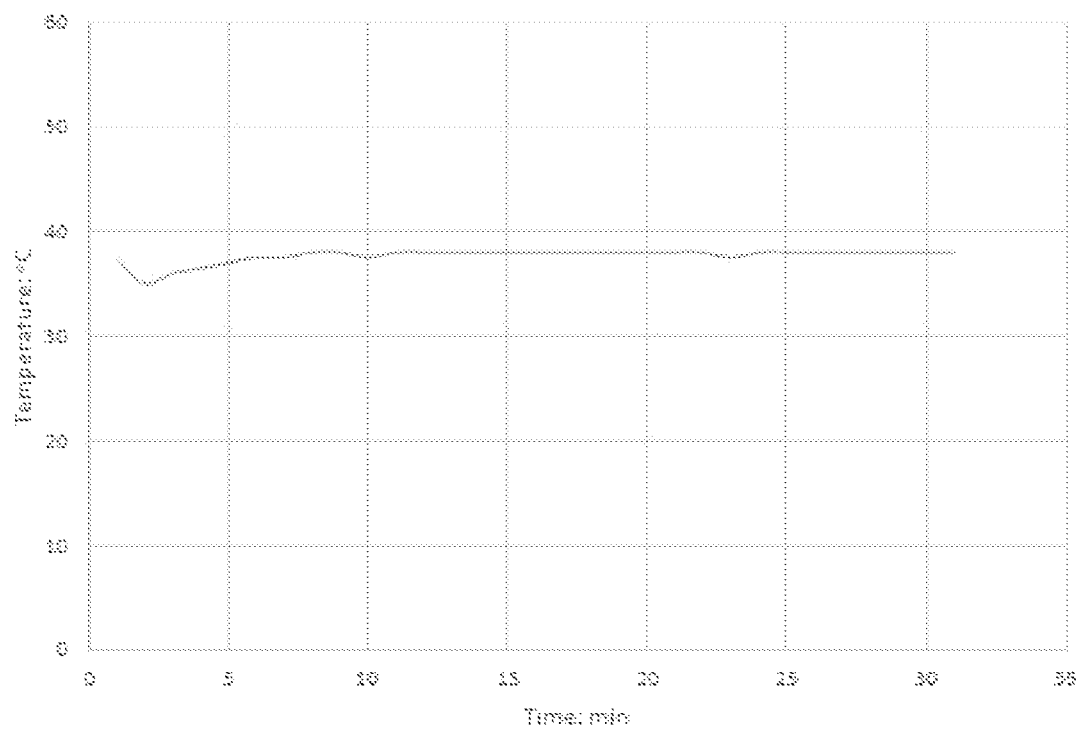

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a polymer" is a reference to one or more polymers and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about: refers to values within 10% of the recited value or range (e.g., about 50 is the equivalent of 45-55).

As used herein, the term "polymer" refers to a chain of repeating structural units or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the term "pre-polymer" refers to linear or branched polymers (e.g., not significantly crosslinked) that have the capacity to be crosslinked under appropriate conditions (e.g., to "cure" and/or form a thermoset or hydrogel), but have not been subjected to the appropriate conditions.

As used herein, the term "crosslinked polymer" refers to a polymer with a significant degree of interconnectedness between multiple polymer strands, the result of which is an insoluble polymer network. For example, multiple polymer stands may be crosslinked to each other at points within their structures, not limited to the ends of the polymer chains.

As used here, the terms "thermoset polymer" and "cured polymer" refer to a polymer network that has exhibits a sufficient degree of covalent crosslinking to render the network insoluble (e.g., in both water and organic solvents) and infusible. "Thermosetting" and/or "curing" may be achieved by thermal (e.g., heating), radiation (e.g., UV crosslinking), or chemical (e.g., chemically-induced crosslinking) means. The thermosetting/curing procedure is not reversible, except by means of chemically breaking the covalent crosslinks.

As used herein, the terms "composite" and "composite material" refer to materials or compositions generated from the combination of two or more constituent materials (e.g., compounds, polymers, etc.). The constituent materials may interact (e.g., non-covalently) at the microscopic or molecular level, but typically do not react chemically (e.g., covalently). At the macroscopic level, the constituent materials typically appear homogenous but may appear separate or distinct.

As used herein, the term "nanoparticles" refers to particles having mean dimensions (e.g., diameter, width, length, etc.) of less than 1 μm (e.g., <500 nm ("sub-500-nm nanoparticles"), <100 nm ("sub-100-nm nanoparticles"), <50 nm ("sub-50-nm nanoparticles"). Nanoparticles may be of any shape and may be two or three dimensional.

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

As used herein, the term "biostable" refers to compositions or materials that do not readily break-down or degrade in a physiological or similar aqueous environment. Conversely, the term "biodegradable" refers herein to compositions or materials that readily decompose (e.g., depolymerize, hydrolyze, are enzymatically degraded, disassociate, etc.) in a physiological or other environment.

As used herein, the term "acrylated" refers to a compound displaying at least one moiety/substituent having the structure:

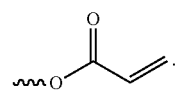

The displayed moiety is referred to as an "acrylate moiety").

As used herein, the term "methacrylteacrylated" refers to a compound displaying at least one moiety/substituent having the structure:

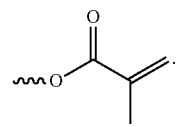

The displayed moiety is referred to as an "methacrylate moiety").

DETAILED DESCRIPTION

Provided herein are thermoresponsive polymer materials and methods of preparation and use thereof. In particular, materials are provided that cure upon exposure to physiologic conditions (e.g., human body temperature) and find use in, for example, orthopedic surgery, bone tissue engineering, and the repair of bone injuries and defects.

In some embodiments, provided herein are thermoresponsive polymer compositions comprising a reactive polymer (e.g., methacrylated polymer (e.g., methacrylated poly(diol citrate), etc.), acrylated polymer (e.g., methacrylated poly (diol citrate), etc.)) and a diazo thermal initiator compound (e.g., V70 (2,2'-Azobis(4-methoxy-2,4-dimethylvaleronitrile), VA-044 (2,2'-Azobis[2-(2-imidazolin-2-yl)propane] dihydrochloride), etc.). In some embodiments, composites of the thermoresponsive polymers described herein and one or more additional components (e.g., a polymer, a bioceramic, etc.) are provided. In some embodiments, the thermoresponsive polymer compositions and composites (e.g., thermoresponsive-polymer/bioceramic composites) thereof cure (e.g., crosslink, transition from a liquid to a solid, transition from soluble to insoluble, etc.) upon exposure to physiologic conditions (e.g., temperature, ionic conditions, etc.). In some embodiments, the compositions and composites herein find use as injectable and/or shape-conforming materials that cure upon exposure to increased temperatures (e.g., physiologic temperatures). Such materials find use in a variety of application, but are of particular use as a scaffold for bone formation, for bone fracture stabilization, for bone tissue engineering, and/or in bone fixation devices.

In some embodiments, polymers that find use are the curable component in the compositions and composites described herein display one or more reactive moieties (e.g., acrylate moiety, methacrylate moiety, etc). In some embodiments, the reactive moieties are stable in the absence of an initiator compound (e.g., diazo initiator, (e.g., V70, VA-044, etc.)). In some embodiments, the reactive moieties are stable in the absence of initiation conditions (e.g., temperatures over 25° C. (e.g., 25° C., 26° C., 27° C., 28° C., 29° C., 30°

C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or more), etc.). In some embodiments, reactive moieties are stable in the absence of an initiator compound (e.g., diazo initiator, (e.g., V70, VA-044, etc.)) and initiation conditions (e.g., physiological conditions (e.g., temperature, ionic concentrations, etc.), etc.). In some embodiments, reactive moieties are stable in the presence of an initiator compound (e.g., diazo initiator, (e.g., V70, VA-044, etc.)) in the absence initiation conditions (e.g., physiological conditions (e.g., temperature, ionic concentrations, etc.), etc.).

In some embodiments, reactive polymers are acrylated polymers. In some embodiments, acrylated polymers display one or more acrylate substituents. In some embodiments, an acrylate substituent is an alkyl acrylate. Examples of alkyl acrylates include methyl acrylate, ethyl acrylate, n-propyl acrylate, isopropyl acrylate, n-butyl acrylate, sec-butyl acrylate, tert-butyl acrylate, lauryl acrylate, cyclohexyl acrylate, dicyclopentenyl acrylate and the like alone or mixtures thereof. In some embodiments, suitable polymers are acrylated by reaction between the polymer and an acrylate compound displaying a suitable moiety (e.g., epoxide moiety) for covalent attachment of the acrylate to one or more positions on the polymer. In some embodiments, glycidyl acrylate is employed to acrylate reactive positions (e.g., hydroxyl, carboxylic acids, etc.) on polymers. In some embodiments, each monomer of a polymer is acrylated. In some embodiments, each occurrence of a particular monomer in a polymer is acrylated (e.g., in a copolymer). In some embodiments, reaction of the acrylate compound (e.g., glycidyl acrylate) with a polymer is controlled (e.g., molar ratio of acrylate to polymer (e.g., 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1,100:1, or ranges therebetween), reaction conditions, reaction time, etc.) to limit the percentage of monomers and/or potentially-acrylatable monomers in a polymer that are acrylated (e.g., %, 2%, 3%, 4%, 5%, 6%, 7%, 8%, 9%, 10%, 15%, 20%, 25%, 30%, 40%, 50%, 60%, 70%, 80%, 90%, or ranges therebetween). In some embodiments, acrylated polymers cure (e.g., crosslink with each other, transition from liquid and/or soluble to solid and/or insoluble) under appropriate conditions (e.g., in the presence of an initiator compound (e.g., V70 and/or VA-40) and/or initiator conditions (e.g., physiological temperature), etc.).

In some embodiments, reactive polymers are methacrylated polymers. In some embodiments, methacrylated polymers display one or more methacrylate substituents. In some embodiments, a methacrylate substituent is an alkyl methacrylate. Examples of alkyl methacrylates include methyl methacrylate, ethyl methacrylate, n-propyl methacrylate, isopropyl methacrylate, n-butyl methacrylate, sec-butyl methacrylate, tert-butyl methacrylate, lauryl methacrylate, cyclohexyl methacrylate, dicyclopentenyl methacrylate and the like alone or mixtures thereof. In some embodiments, suitable polymers are methacrylated by reaction between the polymer and a methacrylate compound displaying a suitable moiety (e.g., epoxide moiety) for covalent attachment of the methacrylate to one or more positions on the polymer. In some embodiments, glycidyl methacrylate is employed to methacrylate reactive positions (e.g., hydroxyl, carboxylic acids, etc.) on polymers. In some embodiments, each monomer of a polymer is methacrylated. In some embodiments, each occurrence of a particular monomer in a polymer is methacrylated (e.g., in a copolymer). In some embodiments, reaction of the methacrylate compound (e.g., glycidyl methacrylate) with a polymer is controlled (e.g., molar ratio of acrylate to polymer (e.g., 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1,100:1, or ranges therebetween), reaction conditions, reaction time, etc.) to limit the percentage of monomers and/or potentially-methacrylatable monomers in a polymer that are methacrylated (e.g., %, 2%, 3%, 4%, 5%, 6%, 7%, 8%, 9%, 10%, 15%, 20%, 25%, 30%, 40%, 50%, 60%, 70%, 80%, 90%, or ranges therebetween). In some embodiments, methacrylated polymers cure (e.g., crosslink with each other, transition from liquid and/or soluble to solid and/or insoluble) under appropriate conditions (e.g., in the presence of an initiator compound (e.g., V70 and/or VA-40) and/or initiator conditions (e.g., physiological temperature), etc.).

In some embodiments, any polymer (or monomer thereof) displaying suitably reactive substituents may find use in embodiments herein. For example, any suitable polymer (or monomer thereof) may be acrylated and/or methacrylated (e.g., as described above and/or in the examples) to produce a reactive polymer that finds use in embodiments herein. For example, suitable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(hexanediol citrate), poly (octanediol citrate), poly(decanediol citrate), poly (dodecanediol citrate), etc.), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), polyethylene, acrylic resins, polyurethane, polypropylene, polymethylmethacrylate, and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). In some embodiments, any of the aforementioned polymers, when modified to display one or more reactive groups (e.g., acrylate, methacrylate, etc.), may find use at the reactive polymer component of materials described herein.

In some embodiments, reactive polymers are citric acid-based polymers. Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98.; U.S. Pat.

Nos. 8,772,437, 8,758,796, 8,580,912, 8,568,765; U.S. Pub. No. 2014/0155516; U.S. Pub. No. 2014/0135407; herein incorporated by reference in their entireties). Depending on the diol of choice, materials with controllable elasticity, biodegradability, and antioxidant properties can be developed (Serrano et al. Adv Mater, 2011. 23(19): p. 2211-5.; Yang J., et al., A thermoresponsive biodegradable polymer with intrinsic antioxidant properties. Biomacromolecules, 2014. 15(11):3942-52.; U.S. Pub. No. 2014/0037588; herein incorporated by reference in its entirety). In some embodiments, polydiolcitrates comprise alternating diol (e.g., linear aliphatic diols) and citrate monomers. In some embodiments, the diol is between 2 and 30 carbons in length (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or ranges therebetween (e.g., 6-16, 7-14, etc.)). In some embodiments, a linear aliphatic diol is X carbons in length and comprises OH substituents at the 1 and X positions (e.g., 1,4-butanediol, 1,6-hexanediol, 1,8-octanediol, 1,10-decanediol, 1,12-dodecanediol, or any terminally-OH-substituted linear aliphatic diol from about 2-20 carbons in length). In certain embodiments, the diol comprises one or more C2-C20 alkyl-diols, C2-C20 alkenyl-diols, or mixtures thereof. In certain other embodiments, the diol comprises one or more C2-C20 alkyl-diols, such as a C6-C20 alkyl-diol, or a C6-C14 alkyl-diol, or a C6-C12 alkyl-diol. For example, the diol comprises an alkanediol, such as 1,12-dodecanediol, 1,10-decanediol, 1,8-octanediol, or a mixture thereof. In another example, the diol comprises 1,10-decanediol, 1,8-octanediol, or a mixture thereof. In another example, the diol comprises 1,8-octanediol (e.g., the polyester is poly(1,8-octanediol-citrate).

In some embodiments, reagents, monomer components of polymers, methods, reaction conditions, etc. that find use in embodiments described herein are described in: U.S. Pat. Nos. 8,911,720, 8,772,437, 8,758,796, 8,580,912, 8,568,765, 8,404,264; U.S. Pub. No. 2014/0058049; U.S. Pub. No. 2013/0211500; U.S. Prov. App. No. 62/160,334; herein incorporated by reference in their entireties.

In some embodiments, materials comprise a poly(glycerol-diacid). A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid)s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), C2-C20 alkyl-diacids, C2-C20 alkenyl-diacids, and mixtures thereof.

In some embodiments, materials and methods herein comprise initiator compounds that induce curing of the reactive polymers described herein (e.g., described in Section II, displaying reactive moieties (e.g., acrylate and/or methacrylate moieties), etc.). In some embodiments, initiators are small molecules that produce free radicals under certain conditions (e.g., temperatures, pH, ionic conditions, etc.). In some embodiments, free radicals are produced by the decomposition of the initiator under certain conditions. In some embodiments, the initiator decomposes to produce free radicals when the decomposition temperature (initiation temperature) is exceeded. In some embodiments, the initiator decomposes to produce free radicals when exposed to an initiation wavelength of light. The free radicals then initiate crosslinking and/or polymerization of reactive moieties. In some embodiments, an initiator is water soluble, oil soluble, soluble is organic solvent, etc. In some embodiments, an initiator is an azo-initiator. Suitable azo initiators are available, for example, from Wako Specialty Chemicals, and include for example:

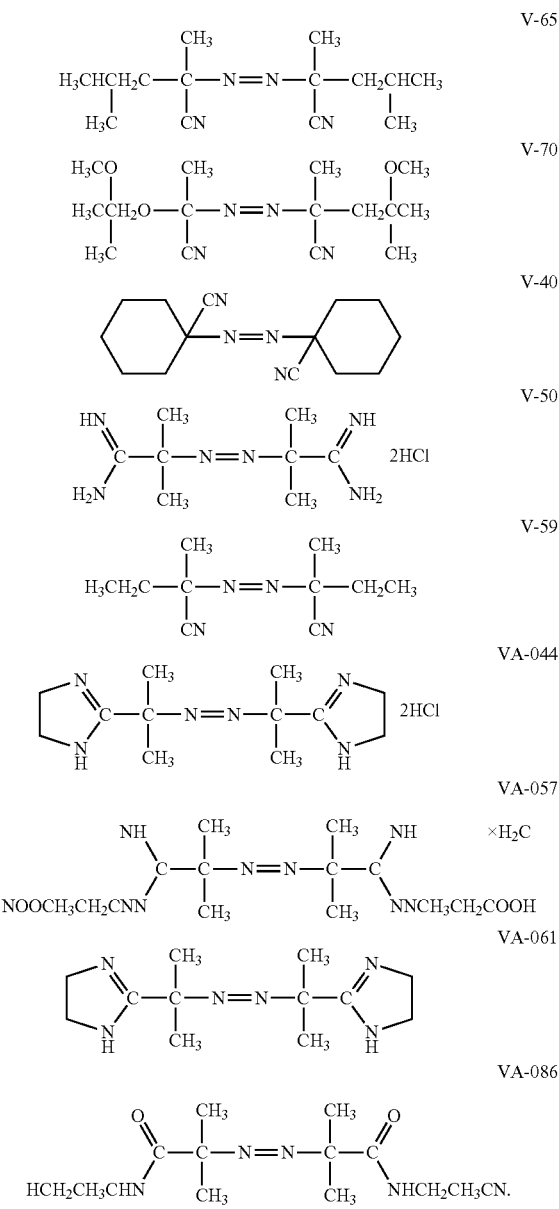

Other examples of suitable initiators include azo-N,N'-bisdimethylvaleronitrile (ABDV), azo-N,N'-bisisobutyronitrile (AIBN), or any other azo-based initiator. In some embodiments, other initiators, such as, peroxides, halogens, metal iodides, metal alkyls, persulfates, etc. find use in embodiments herein, to the extent that they initiate curing of reactive polymers under desired conditions (e.g., temperatures).

In some embodiments, materials described herein comprise composites of the thermoresponsive polymer materials described herein and one or more additional components (e.g. in additional to initiator compounds). In some embodiments, additional components comprise 1-99 wt % of the composite material (e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or ranges therebetween).

In some embodiments, a thermoresponsive composite material comprises at least 1% (e.g., >>1%, >2%, >3%, >4%, >5%, >10%, >20%, >30%, >40%, >50%, >60%, >70%, >80%, >90%, >95%, >98%, >99%) thermoresponsive polymer (e.g., citrate-based polymer (e.g., methacrylated poly(diol citrate), etc.)). In some embodiments, a thermoresponsive composite material comprises less than 99% (e.g., <99%, <98%, <95%, <90%, <80%, <70%, <60%, <50%, <40%, <30%, <20%,<10%, <5%,<4%, <3%, <2%, <1%) thermoresponsive polymer (e.g., citrate-based polymer (e.g., methacrylated poly(diol citrate), etc.)). In some embodiments, a thermoresponsive composite material comprises thermoresponsive polymer (e.g., citrate-based polymer (e.g., methacrylated poly(diol citrate), etc.)) in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, or ranges therebetween. The aforementioned percentages may be wt % or molar %.

In particular embodiments, composites of thermoresponsive citrate-based polymer materials and a bioceramic component are provided. Suitable bioceramics include hydroxyapatite (HA; $Ca_{10}(PO_4)_6(OH)_2$), tricalcium phosphate beta (β TCP; $Ca_3(PO_4)_2$), and mixtures of HAP and β TCP. In some embodiments, bioceramic nanoparticles and/or bioceramic microparticles find use in embodiments herein and/or are a component of a composite material within the scope herein. In some embodiments, a thermoresponsive composite comprises (1) a citrate-based polymer component (e.g., methacrylated poly(diol citrate), etc.), (2) an initiator (e.g., V70, VA-044, etc.), and (3) a bioceramic component (e.g., bioceramic nanoparticles and/or bioceramic microparticles). In some embodiments, the bioceramic component comprises 1-99 wt % of the thermoresponsive composite material (e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or ranges therebetween (e.g., 5-65 wt %, 10-60 wt %, 20-50 wt %, etc.). In some embodiments, the bioceramic (e.g., HA, β TCP, etc.) component comprises bioceramic nanoparticles. In some embodiments, the mean diameter of nanoparticles used in embodiments herein is less than 1 μm (e.g., 900 nm, 800 nm, 700 nm, 600 nm, 500 nm, 400 nm, 300 nm, 250 nm, 200 nm, 150 nm, 100 nm, 75 nm, 50 nm, 25 nm, 20 nm, 15 nm, 10 nm, or less, or ranges therebetween).

In some embodiments, composite materials comprise one or more additional polymeric components (e.g., in addition to the citrate-based polymer component (e.g., methacrylated poly(diol citrate)). Suitable biodegradeable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly (hydroxyl acids), poly(L-lactide) poly(D,L lactide), poly(D, L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). Suitable non-biogregradable polymers include silicone rubber, polyethylene, acrylic resins, polyurethane, polypropylene, and polymethylmethacrylate.

In some embodiments, polymers are obtained and/or prepared according to standard techniques. For example, methods and materials for synthesis of poly(diol citrate) polymers and related polymers (e.g., further comprising glycerol or other additional monomers) are described in the literature, such as Yang et al. (Biomaterials. 2006 March; 27(9):1889-98.; incorporated by reference in its entirety) and other patents and publications incorporated herein by reference in their entireties. In some embodiments, to synthesize poly(diol citrate) polymer, approximately equimolar amounts of citric acid and diol (e.g., linear aliphatic diol, terminal-OH diols, one diol species, multiple diol species, etc.) are melted together (e.g., under inert (e.g., nitrogen) atmosphere, at about 165° C., etc.) with stirring (e.g., for 20 min). The temperature is subsequently decreased to an appropriate polymerization temperature (e.g., about 140° C.) and the mixture is stirred (e.g., for 30-120 min) to obtain the poly(diol citrate) pre-polymer. In some embodiments, the pre-polymer is dissolved in ethanol, purified in Milli-Q water, and/or lyophilized to dryness. Related polymers (e.g., comprising additional monomers and/or substituents) are prepared using similar methods that are understood in the field and/or in references incorporated herein. Other polymers that find use in embodiments herein are obtained and/or prepared using available methods and the disclosure herein.

In some embodiments, polymers are selected having reactive side groups that facilitate curing of the polymers, induced by an initiator compound and/or initiation conditions. In other embodiments, polymers (e.g., selected for their physical/mechanical characteristics) are modified to display reactive groups (e.g., acrylates, methacrylates, etc.). For example, in some embodiments, acrylate and/or methacrylate groups are added to polymers by reacting the polymers with a glycidyl methacrylate compound, glycidyl acrylate, or other acrylate/methacrylate-displaying reactive compounds. In some embodiments, methacrylated poly(diol citrates) are synthesized using methods and reagents understood in the field and/or described in the literature, for example, Wang et al. (Biomater Sci. 2013 June; 1(6):625-632.; incorporated by reference in its entirety). In particular embodiments, poly(diol citrate) pre-polymer is methacrylated by dissolving the prepolymer in tetrahydrofuran, adding imidazole and then glycidyl methacrylate. The mixture is stirred under heat (e.g., about 60° C.). Solvent is removed (e.g., by rotary evaporation). The resulting methacrylated poly(diol citrate) may be purified in Milli-Q water and lyophilized to dryness. Acrylated poly(diol citrates) (aP(DC)s) are synthesized using analogous methods and reagents. Related polymers (e.g., comprising additional monomers and/or substituents) are acrylated/methacrylated using similar methods that are understood in the field and/or in references incorporated herein. Other polymers that find use in embodiments herein are acrylated/methacrylated using available methods. Other reactive groups may be added to polymers (e.g., poly(diol citrate)s or other polymers) using available chemistries and the disclosure herein.

In some embodiments, reactive polymers (e.g., acrylated/methacrylated polymers (e.g., methacrylated poly(diol citrate), etc.) are rendered curable by mixing with a sufficient amount of an initiator compound (e.g., diazo compound). In some embodiments, the reactive polymer and the initiator compound are mixed together in the absence of solvent. In some embodiments, the reactive polymer and the initiator compound are mixed together in the presence of solvent (e.g., water, organic solvent (e.g., ethanol, ethyl; acetate, etc.). In some embodiments, an appropriate accelerator (e.g., based on the identity of the polymer, reactive groups, initiator, etc.), such as a tertiary amine (e.g., ethyl 4-dimethylaminobenzoate (EDAB), etc.), is included. In some embodiments, CuO nanoparticles (e.g., 20-100 nm diameter (e.g., 20, 30, 40, 50, 60, 70, 80, 90, 100, or ranges therebetween)) and/or CaOP are included (e.g., with or without EDAB) as an accelerator to increase curing rate and/or enhance the mechanical properties of the resulting composite. In some embodiments, an accelerator is not included. For example, in some embodiments, a methacrylated poly(diol citrate) pre-polymer is rendered curable by dissolving the soluble pre-polymer in solvent (e.g., ethyl acetate) and adding an appropriate amount of initiator (e.g., V70) and optionally, accelerator (e.g., EDAB). Following mixing of the components, the poly(diol citrate) pre-polymer is rendered curable (e.g., when placed under curing conditions (e.g., physiologic conditions), the material will auto-cure). In some embodiments, related polymers (e.g., comprising additional monomers and/or substituents) are rendered curable using similar methods that are understood in the field and/or in references incorporated herein. Other polymers that find use in embodiments herein are rendered curable using available methods and the disclosure herein.

In some embodiments, reactive polymers (or pre-polymers) are combined with another component (e.g., secondary polymer, bioceramic, etc.) to form a composite. In some embodiments, reactive polymers (or pre-polymers) and initiator are combined with another component (e.g., secondary polymer, bioceramic, etc.) to form a curable composite. In some embodiments, reactive polymer is combined with initiator to produce a curable polymer, which is subsequently combined with an additional component (e.g., secondary polymer, bioceramic, etc.) to form a curable composite. In some embodiments, reactive polymer is combined with an additional component (e.g., secondary polymer, bioceramic, etc.), which is subsequently combined with an initiator to form a curable composite. In some embodiments, multiple additional components (e.g., secondary polymer, bioceramic, etc.) are added. For example, in some embodiments, curable bioceramic/poly(diol citrate) composites are synthesized by sequentially mixing the different components. For example, first, the appropriate amount of solvent (e.g., ethyl acetate) and optionally accelerator (e.g., EDAB) are added to the reactive polymer (e.g., methacrylated poly (diol citrate). Next, the components are mixed to homogeneity (e.g., using a vortex mixer). Then, bioceramic (e.g., a hydroxyapatite nanopowder) is added and the components are mixed thoroughly. Finally, the thermal initiator (e.g., V70) is added and the components are mixed thoroughly. The result is a curable composite. In other embodiments, the order of addition is altered. In some embodiments, all components are mixed in a single step. In some embodiments, composites of related polymers (e.g., comprising additional monomers and/or substituents) are prepared using similar methods that are understood in the field and/or in references incorporated herein. Composites of other polymers that find use in embodiments herein are prepared using available methods and the disclosure herein.

As described throughout, provided herein are materials comprising curable (e.g., thermoresponsive) polymers and composites thereof. These materials find use in a variety of applications. For example, any application in which it is desired that a material be applied in a liquid and/or soluble form, and then is (rapidly) rendered solid and/or insoluble when exposed to desired conditions (e.g., physiological temperature). Materials described herein find use, for example, in medical and dental bone repair applications, such as, repair of craniofacial injuries, stabilizing complex fractures, promoting bone growth, bone regeneration, as a bone-void filler, adhering implants, etc. In some embodiments, materials find use in non-medical/dental applications.

In some embodiments in which the materials herein are used for the repair, stabilization, regeneration, growth, etc. of bone or bone fractures/injuries, the materials further comprise additional components/agents to facilitate incorporation into bone, bone growth, bone regeneration, etc. In some embodiments, additional components/agents are incorporated into the materials and are subsequently encapsulated within the material upon curing. In such embodiments, additional components/agents are non-covalently associated with the polymer and other components of the materials. In other embodiments, additional components/agents are covalently-linked to the reactive polymer and/or other components (e.g., bioceramic) of the material.

In some embodiments, the materials described herein find use in the delivery of growth factors or other bioactive agents for the repair of bone defects and/or regeneration of bone. Suitable agents for use in embodiments herein include bone morphogenic proteins (e.g., BMP-1, BMP-2, BMP-4, BMP-6, and BMP-7); members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); vascular endothelial growth factor (VEGF); fibroblast growth factor (FGF); etc. These agent, or others, may be covalently linked to materials described herein or components thereof, non-covalently associated with moieties displayed on materials described herein or components thereof, embedded within materials described herein, etc.

Experimental

Materials and Methods

Reagents

All chemicals were purchased from Sigma and used without further purification except where indicated otherwise.

Fabrication of Poly Diol Citrate-HA Nanocomposites, mPOC and mPDC

Equimolar amounts of citric acid and 1,8-octanediol were added to a round-bottom flask and melted together under nitrogen atmosphere at 165° C. with stirring for 20 min. The temperature was subsequently decreased to 140° C. and the mixture was stirred for 72 min to obtain the POC pre-polymer. Shortly after, the pre-polymer was dissolved in ethanol, purified in Milli-Q water and lyophilized for 24 hr. POC was methacrylated by dissolving 66 g of POC in 540 mL of tetrahydrofuran. After dissolution, 2448 mg of imidazole was added, followed by drop-wise addition of 53.3 mL of glycidyl methacrylate. The mixture was stirred for 6 hr at 60° C. in a round-bottom flask. Then, the solvent was removed by 30 min of rotary evaporation at 60° C. The resulting methacrylated poly(octamethylene citrate) (mPOC) was purified in Milli-Q water and lyophilized for 12 hr.

Poly(dodecamethylene citrate) (PDDC) was synthesized by the polycondensation of citric acid and 1,12-dodecanediol (2:1 molar ratio). Citric acid and 1,12-dodecanediol were heated to 165° C. under nitrogen atmosphere. After melting, the reaction was continued for an additional 30 min at 140° C. The PDDC pre-polymer was then dissolved in ethanol, purified in Milli-Q water and lyophilized for 24 hr. Next, PDDC was methacrylated by employing the same procedure used to methacrylate POC. The mass ratios of the different ingredients were kept the same.

The hydroxyapatite composites were synthesized by sequentially mixing the different components. First, the appropriate amount of ethyl acetate and ethyl 4-dimethylaminobenzoate (EDAB) added to either mPOC or mPDC. Then, the components were mixed to homogeneity using a vortex mixer. Afterwards, hydroxyapatite nanopowder was added and mixed thoroughly using a vortex mixer. Finally, the thermal initiator, V70, was added and mixed using a vortex mixer. The mixture was then used immediately for experiments. The materials can also solidify in the absence of the accelerator EDAB.

TABLE 1

Composition of the six formulations tested. The weight percentages were calculated based on the total mass of the final mixture. The initiator (V70) and accelerator, ethyl 4-dimethylaminobenozate (EDAB), amounts were optimized to yield a formulation setting time of approximately fifteen minutes. The ethyl acetate (EtOAc) weight percentage was determined to be the minimum amount required to dissolve all the components and retain injectability.

| Formulation | V70 wt. % | EDAB wt. % | Nano-HA wt. % | EtOAc wt. % |
|---|---|---|---|---|
| mPOC | 1 | 2 | — | 5 |
| mPOC-20HA | 1 | 2 | 20 | 5 |
| mPOC-40HA | 2 | 2 | 40 | 5 |
| mPDC | 2 | 2 | — | 10 |
| mPDC-20HA | 3 | 3 | 20 | 10 |
| mPDC-40HA | 3 | 4 | 40 | 10 |

Polymer Chemical Characterization

The proton nuclear magnetic resonance ($^1$H-NMR) spectra of POC, mPOC, PDDC, and mPDC were recorded with an Au400 NMR spectrometer (Agilent, Santa Clara, CA) at ambient temperature, using dimethylsulfoxide-$d_6$ as a solvent and a reference. Fourier transform infrared (FT-IR) transmission spectra were recorded in attenuated total reflectance mode on a Nicolet Nexus 870 spectrometer (Thermo Scientific, Waltham, Mass.) by accumulation of 32 scans, with a resolution of 8 cm$^{-1}$.

Maximum Temperature Reached During Cross-Linking Process

The maximum temperature during free-radical polymerization was measured with a Thermocouple Data Logger (OMEGA Engineering, Stamford, Connecticut). A K-type thermocouple was inserted into a Teflon Exothermic Heat Mold (FIG. 1, ASTM F451). The mold was pre-heated to 37° C. Then, 10 mL of each tested formulation was poured into the mold. The temperature was recorded until it returned to the baseline temperature of 37° C.

Gel Point

The gel point corresponding to the onset of the formation of a polymer network was measured using rheology. The thermosetting mixture was placed in a disposable aluminum dish attached to the temperature controlled plate of a rheometer (model MCR 302, Anton Paar, Ashland, VA). A cylindrical, stainless-steel parallel geometry of 8 mm diameter was lowered until the measurement gap was 1 mm. The starting temperature of the material was 20° C. The temperature of the Peltier plate was 37° C. The oscillatory program consisting of a time sweep at an oscillatory frequency of 10 rad/s and magnitude of 0.5% strain was used to monitor the viscosity as the composite cured. The gel point was recorded as the time when the polymer viscosity suddenly increased; order of magnitude change.

Characterization of Mechanical Properties

The mechanical properties of the formulations were determined by using an MTS Sintech 20 g universal mechanical testing machine with a 100 kN load cell. The compression tests were performed in accordance with the protocols described in ASTM F451. Cylindrical specimens (6 mm diameter, 12 mm height) were synthesized by curing the tested formulations for 24 hr in a steel compression specimen mold (ASTM F451 dimensions) heated to 37° C. The cylinders were then compressed at a rate of 20 mm/min. The ultimate compressive strength and the modulus were calculated after correcting for the compliance of the testing machine.

TABLE 2

Summary of mechanical characteristics

| Formulation | Modulus (GPa) | Ultimate compressive strength (MPa) | Strain (%) at failure |
|---|---|---|---|
| mPOC (n = 5) | 0.791 ± 0.102 | 220 ± 27.6 | 49.7 ± 1.68 |
| mPOC-20HA (n = 5) | 0.604 ± 0.0393 | 183 ± 8.86 | 46.8 ± 1.11 |
| mPOC-40HA (n = 5) | 0.647 ± 0.0725 | 124 ± 14.4 | 34.1 ± 2.58 |

In Vitro Degradation of Poly Diol Citrate-HA Nanocomposites

Cylindrical specimens (6 mm in diameter and 12mm in height) were placed in a 15 mL conical tube containing 5 mL 0.5 M NaOH to rapidly obtain relative degradation rates among samples. Specimens were weighed, and then incubated at 37° C. in NaOH solution for predetermined times. After incubation, samples were washed with water and freeze-dried for 72 hr. Mass loss was calculated by comparing the initial mass ($W_0$) with the mass measured at a given time point ($W_t$), as shown in Eq. (1). Five individual experiments were performed for the degradation test. The results are presented as means±standard deviation.

$$\text{Mass loss (\%)} = \frac{W_0 - W_t}{W_0} \times 100. \quad (1)$$

Scanning Electron Microscopy

The surface morphology of the degrading samples was observed at each time point via scanning electron microscopy (SEM) (Hitachi S4800-II cFEG SEM).

In Vivo Biocompatibility of Poly Diol Citrate-Hydroxyapatite Nanocomposites

All animal procedures were performed in accordance with the Guide for the Care and Use of Laboratory Animals published by the National Institutes of Health (NIH Publication 85-23, 1996) and approved by Northwestern University Animal Care and Use Committee. Three 100 μL subcutaneous injections were given to male Sprague Dawley rats between 175-200 g to evaluate the foreign body response of the developed formulations. Animals were anesthesized with isoflurane (2-3%). Then, the bac of the rat was shaved and sterilized (i.e. betadine, alcohol). Before performing any injections, the animals were treated preoperatively with buprenorphrine subcutaneously 0.05 mg/kg for pain control. The first injection was a clinically available poly(methyl methacrylate) (PMMA) bone cement (Simplex P SpeedSet™ Radiopaque Bone Cement, Stryker, Kalamazoo, MI). The second injection was a polymer-only formulation (i.e. mPOC or mPDC). The third injection was a polymer-ceramic composite containing 40% hydroxyapatite (i.e. mPOC-40HA, mPDC-40HA). After each injection, the site was marked with a permanent marker for tracking purposes. The animals were sacrificed at correspondingly different times for hardness testing and histology.

Figure 8A:
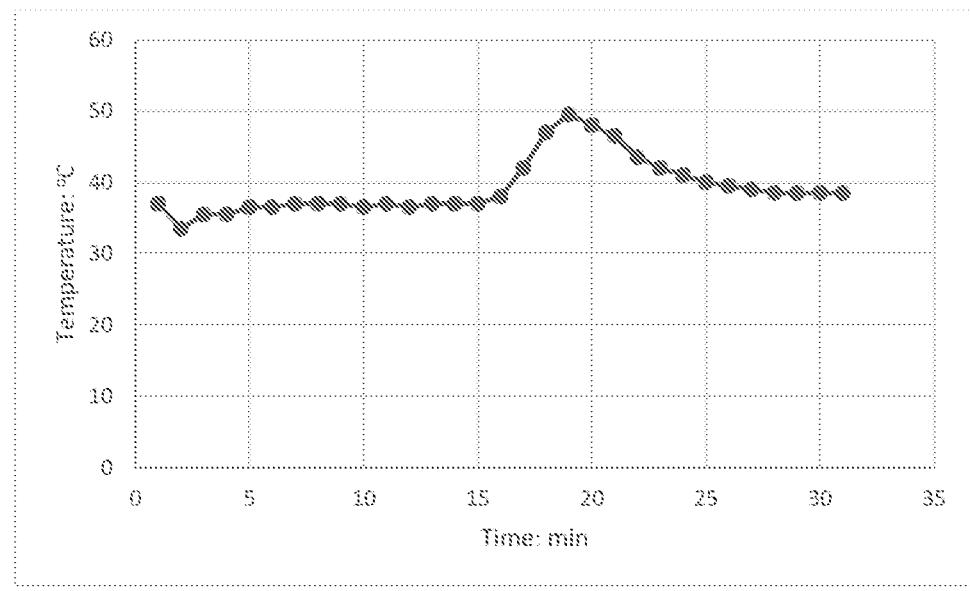
FIG. 8A-D. Graphs depicting material temperature during curing for (A) mPOC, (B) mPOC-40HA, (C) mPDC, and (D) mPDC-40HA.
Figure 8B:
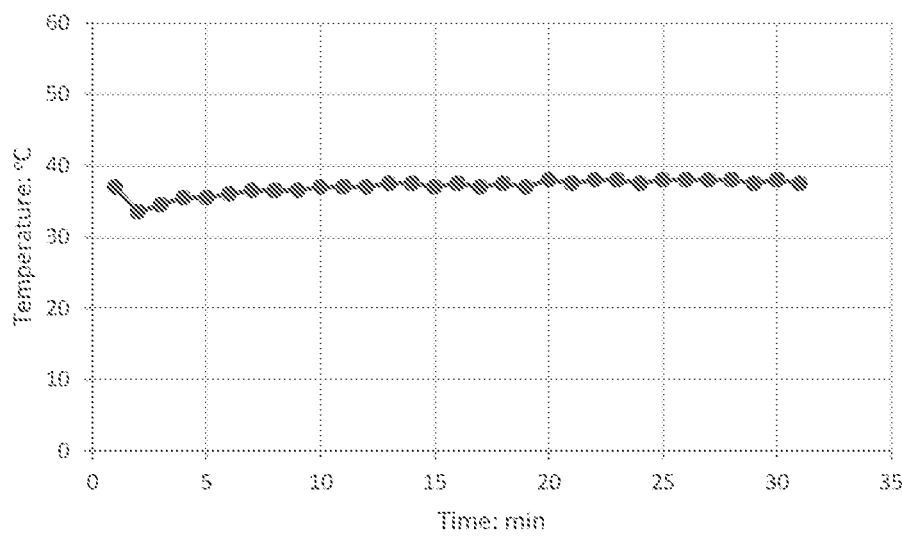
Figure 8C:
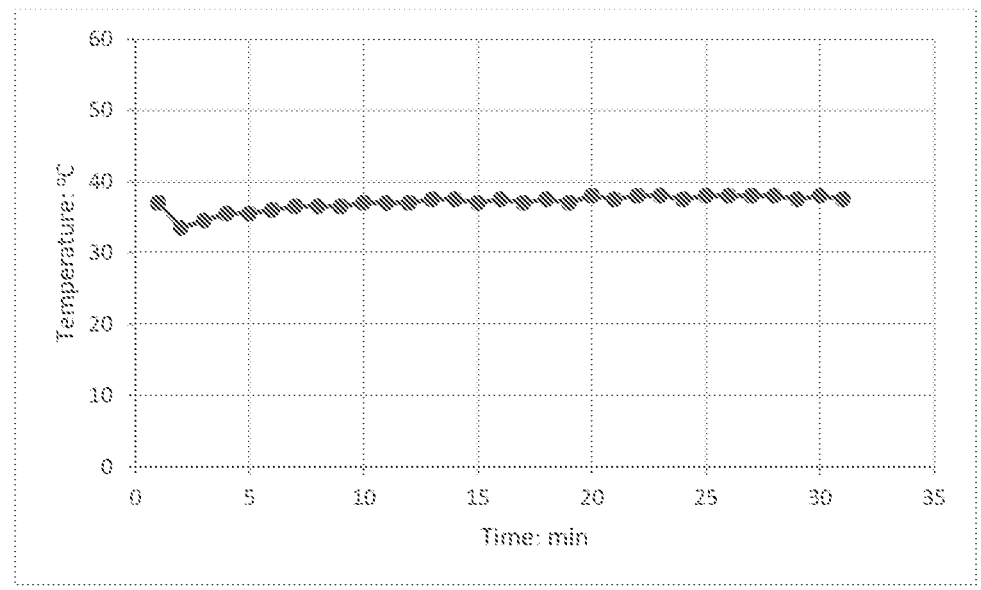
Figure 8D:
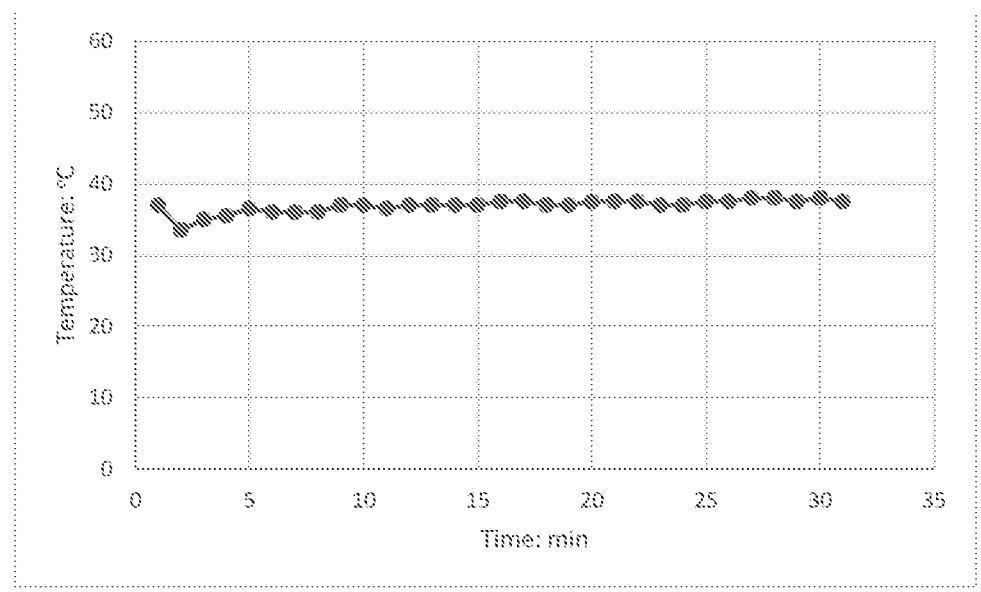

Characterization of the Exothermic Reaction During Curing of Composites that Contain V70 Initiator and EDAB Accelerator FIG. 8 depicts polymer temperatures during curing for mPOC (FIG. 8A), mPOC-40HA (FIG. 8B), mPDC (FIG. 8C), and mPDC-40HA (FIG. 8D). Polymer was cured in a round mold with 9 mm diameter and 5 mm height at 37° C. for 30 min. Temperature was recorded by EasyLog. Maximum temperatures ranged from 38-53° C. and were achieved at 10-18 minutes.

Benzoyl Peroxide (BPO) Initiator Cures both mPDC and mPOC Polymer

Figure 9A:
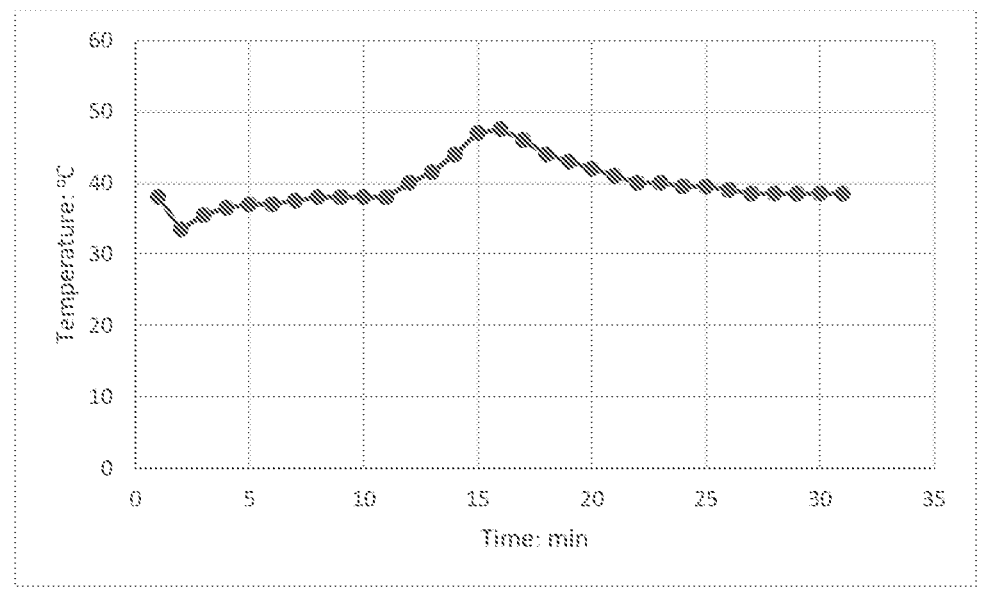
FIG. 9A-B. Graphs depicting material temperature during curing in the presence of BPO initiator for (a) mPOC and (b) mPOC-40HA.
Figure 9B:
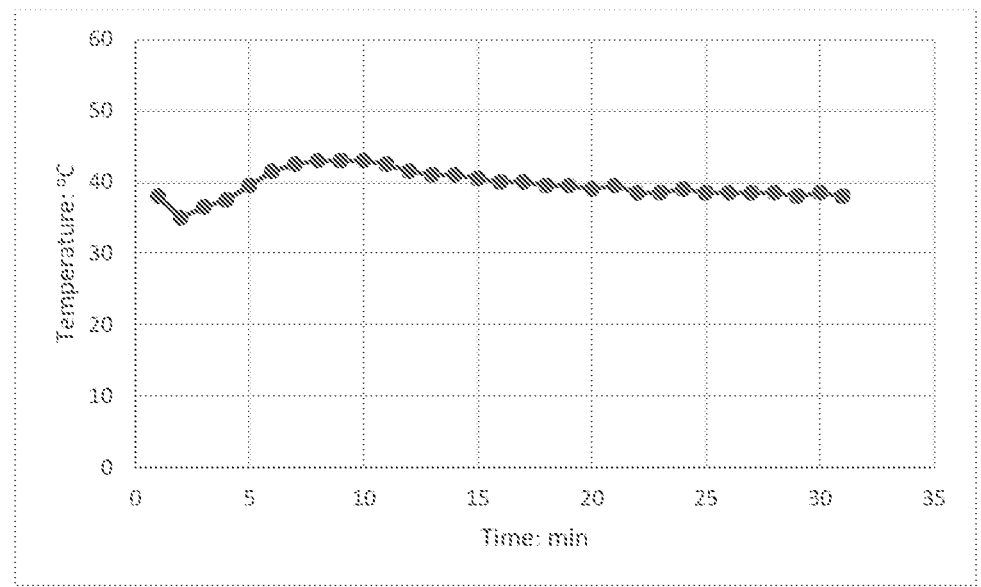

BPO initiator induces the exothermic curing of mPDC (FIG. 9A) and mPOC (FIG. 9B).

V70 Cures Both mPDC and mPOC Polymers without the Accelerator

Figure 10A:
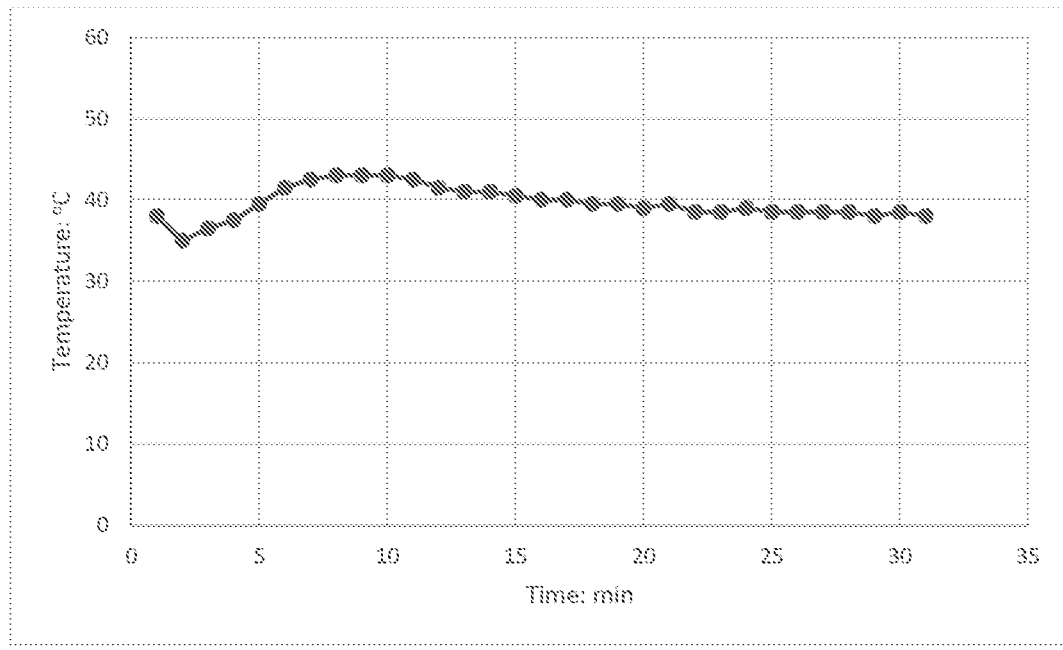
FIG. 10A-B.
Figure 10B:
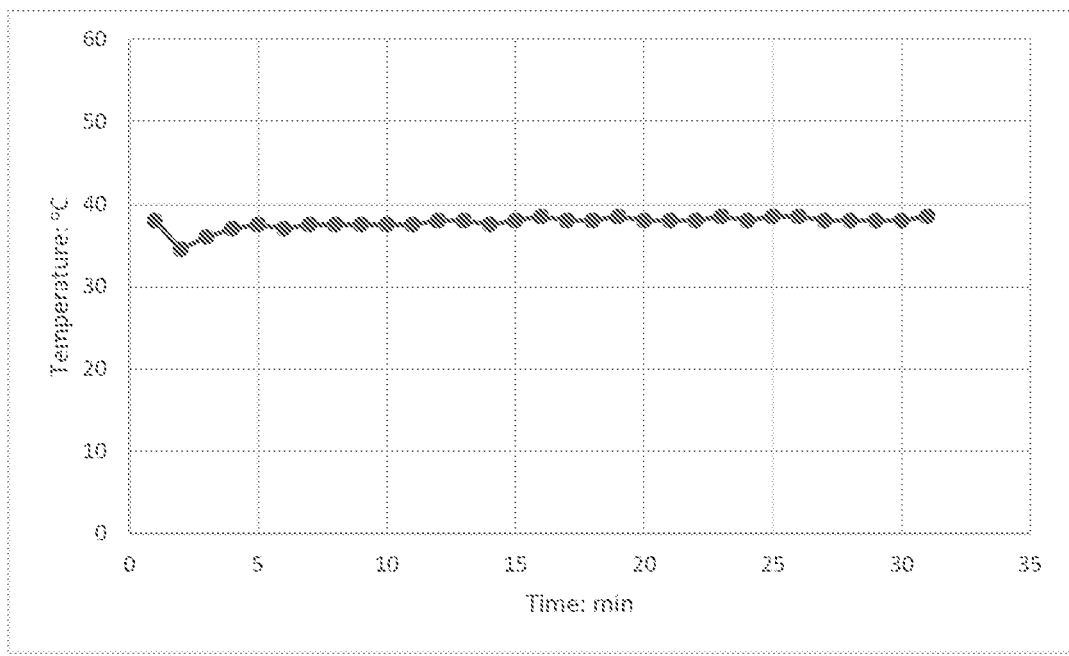

V70 initiator induces the exothermic curing of mPOC (FIG. 10A) and mPDC-40HA (FIG. 10B) without the addition of accelerator.

Figure 11:
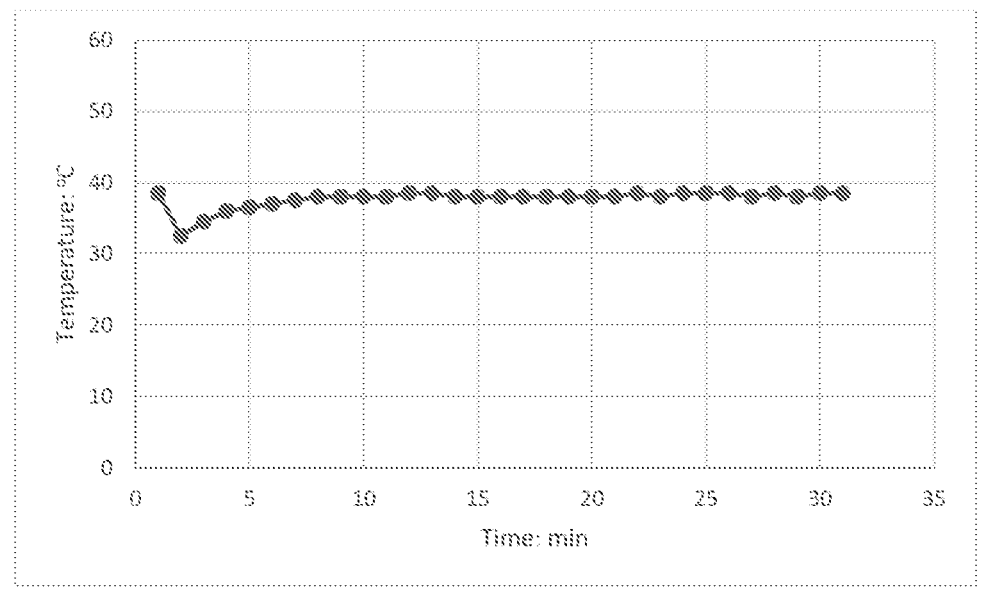
FIG. 11. Graph depicting temperature during curing in the presence of V70 initiator mPOC-40HA, after being stored at -20° C. overnight.
Figure 12A:
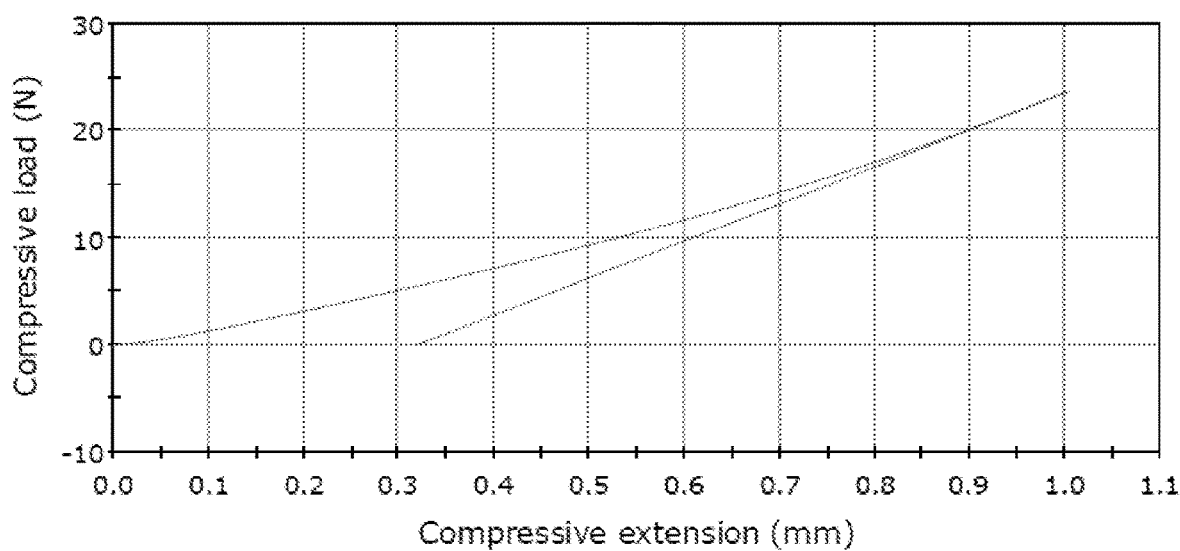
FIG. 12A-E. Graphs and tables depicting the results of compression testing.
Figure 12B:
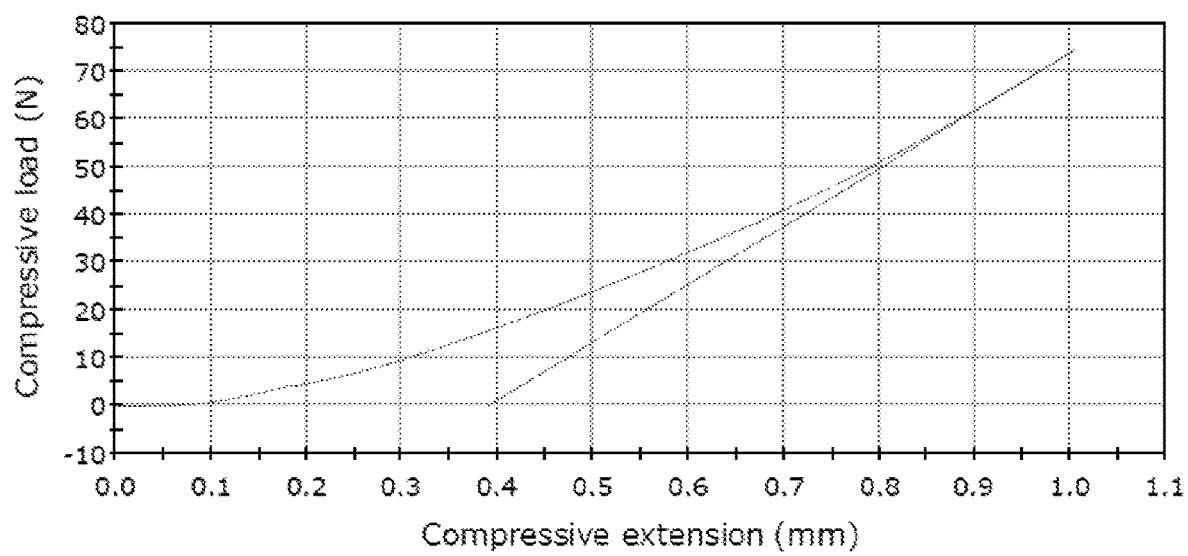
Figure 12C:
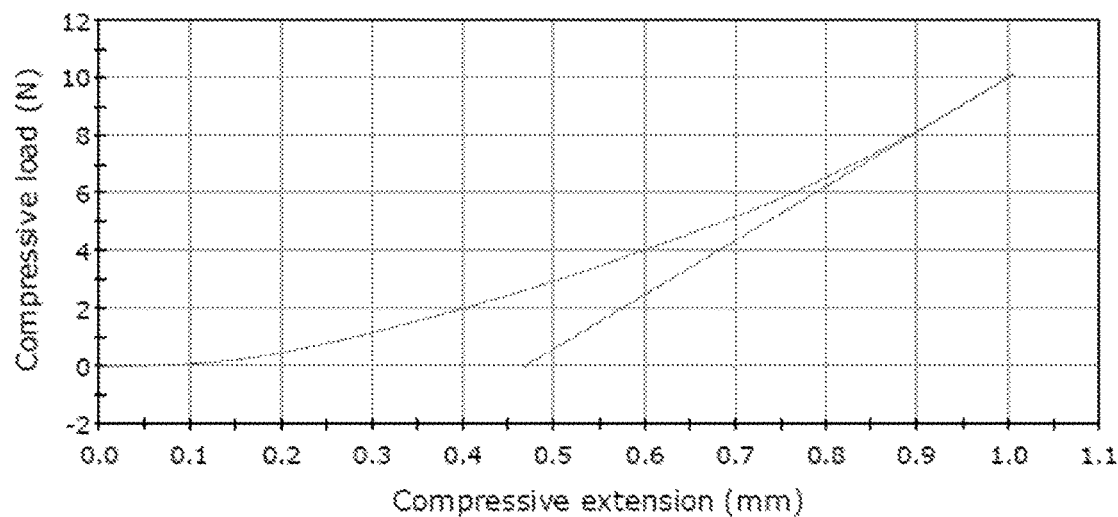
Figure 12D:
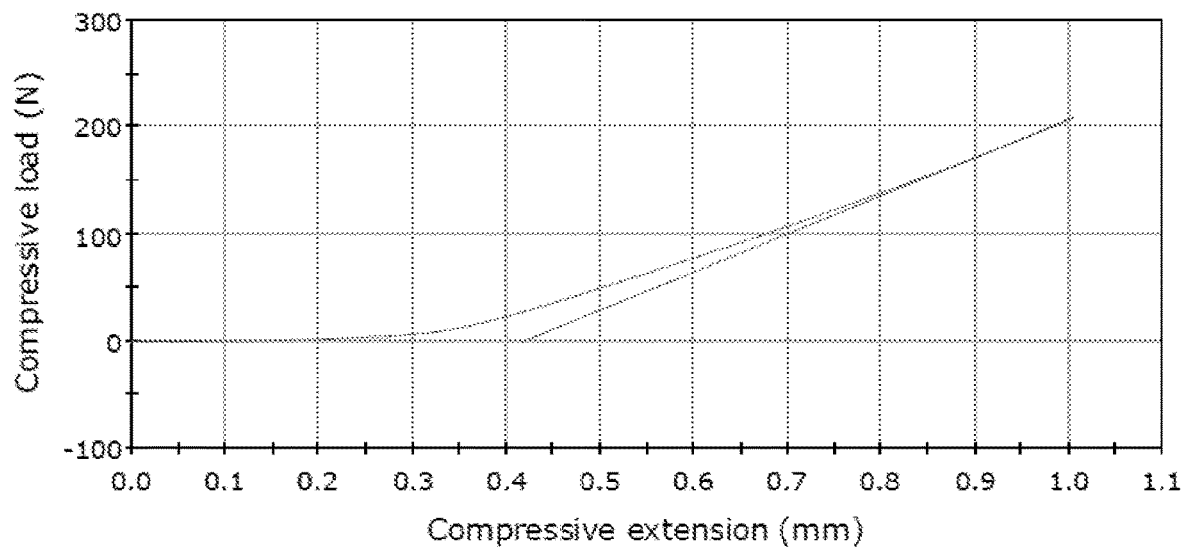
Figure 12E:
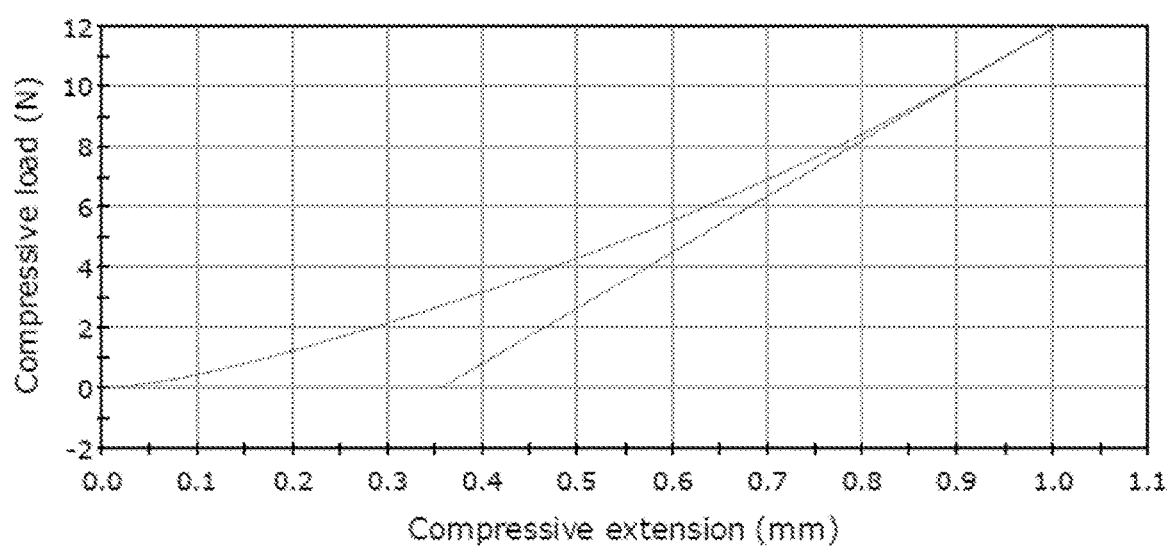
Figure 13A:
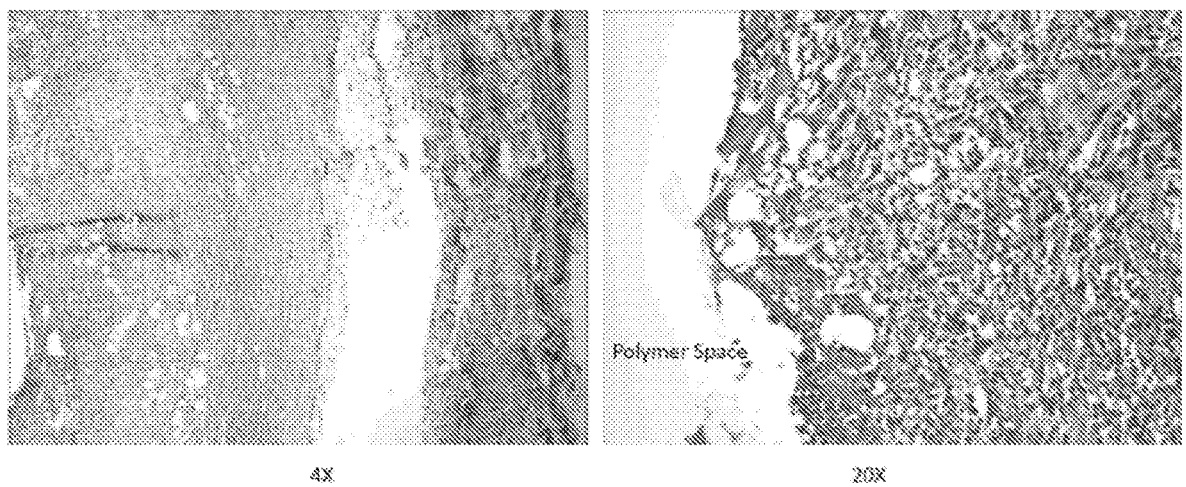
FIG. 13A-D. Images depicting two-week biocompatibility in subcutaneous rat tissue, using HE stain.
Figure 13A:
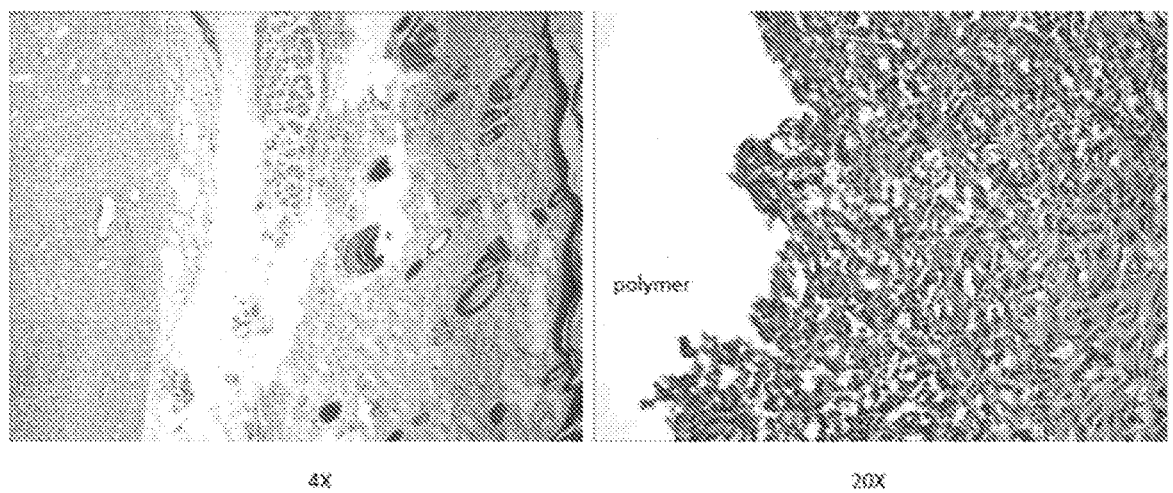
Figure 13B:
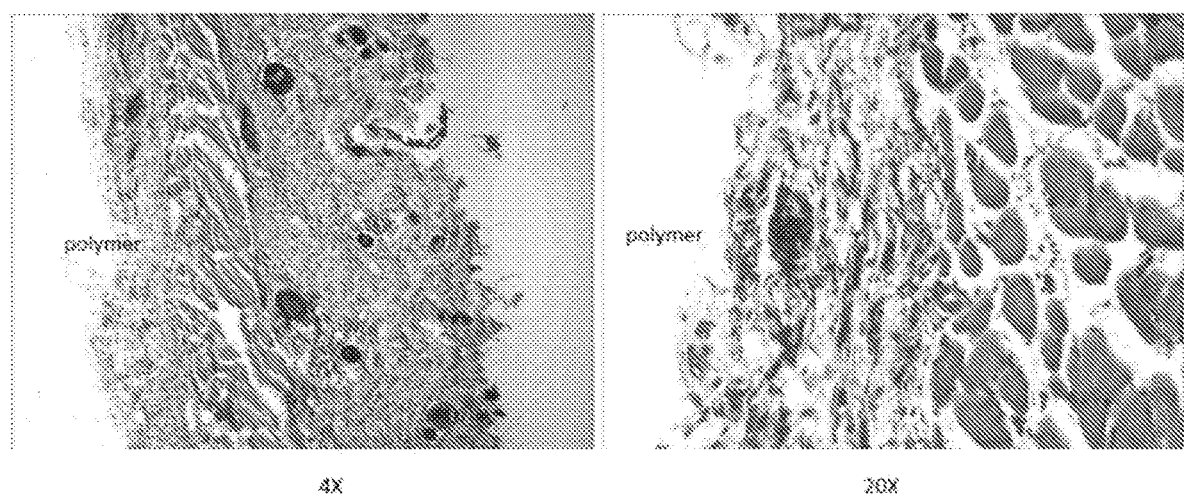
Figure 13B:
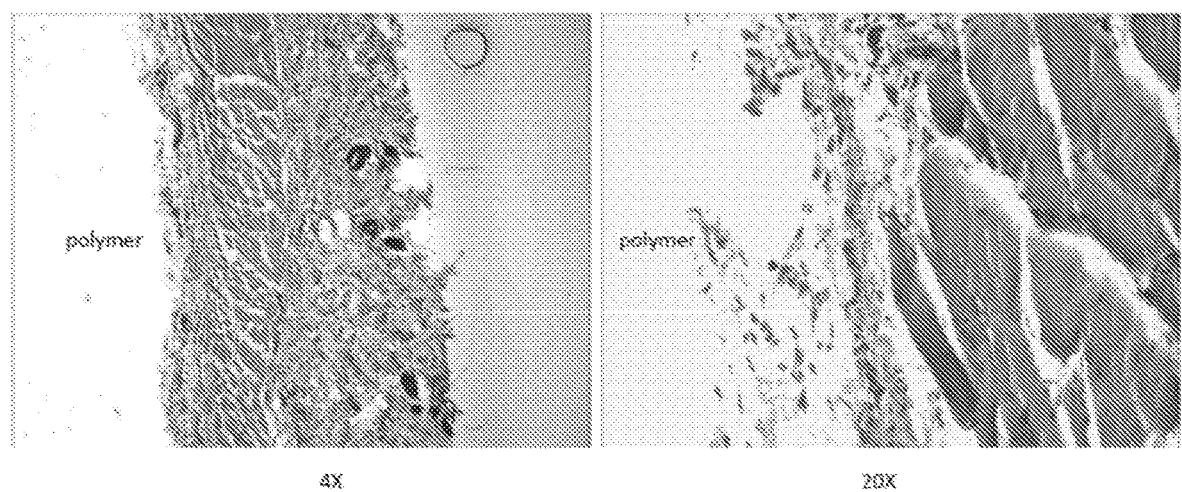
Figure 13C:
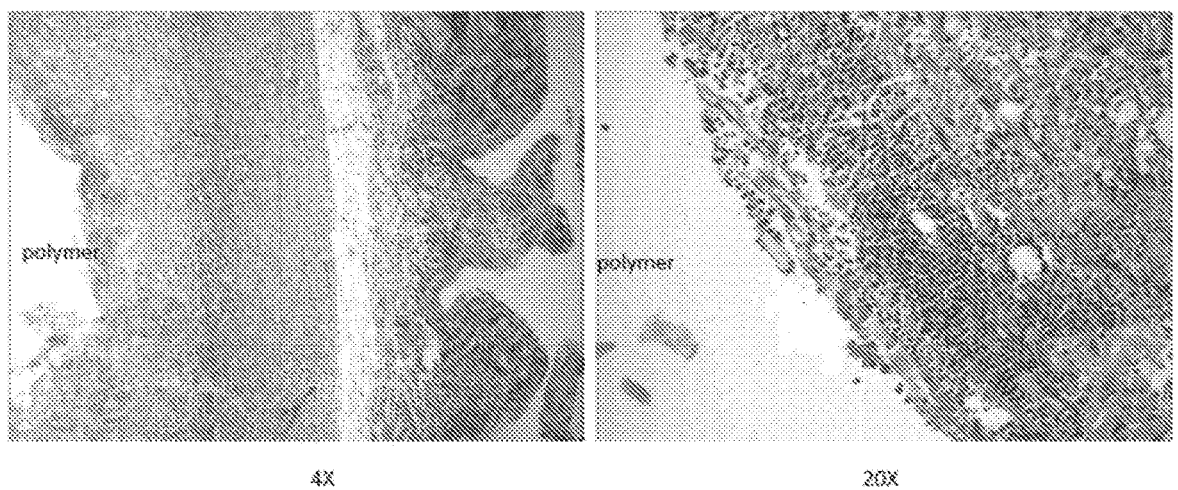
Figure 13C:
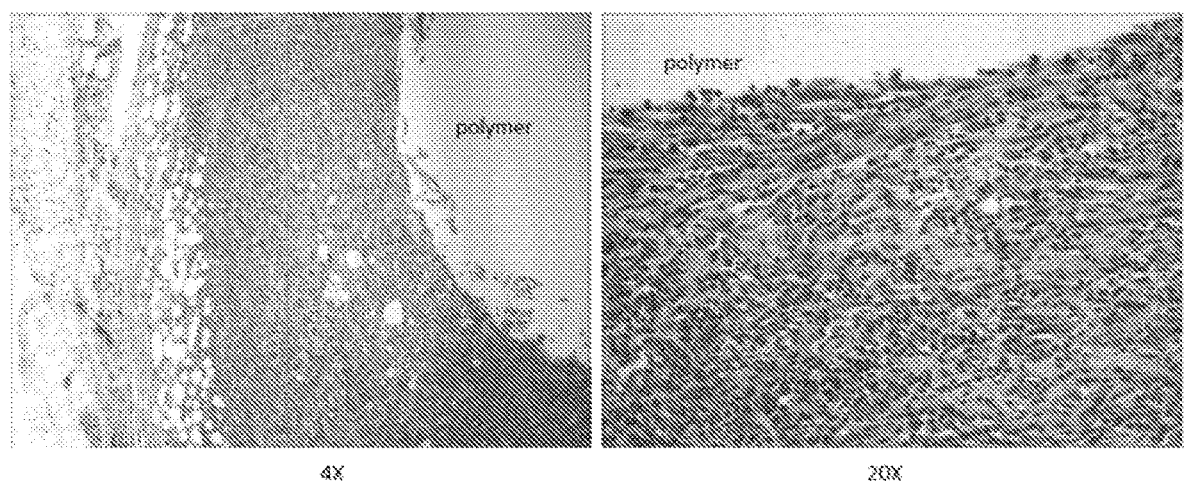
Figure 13D:
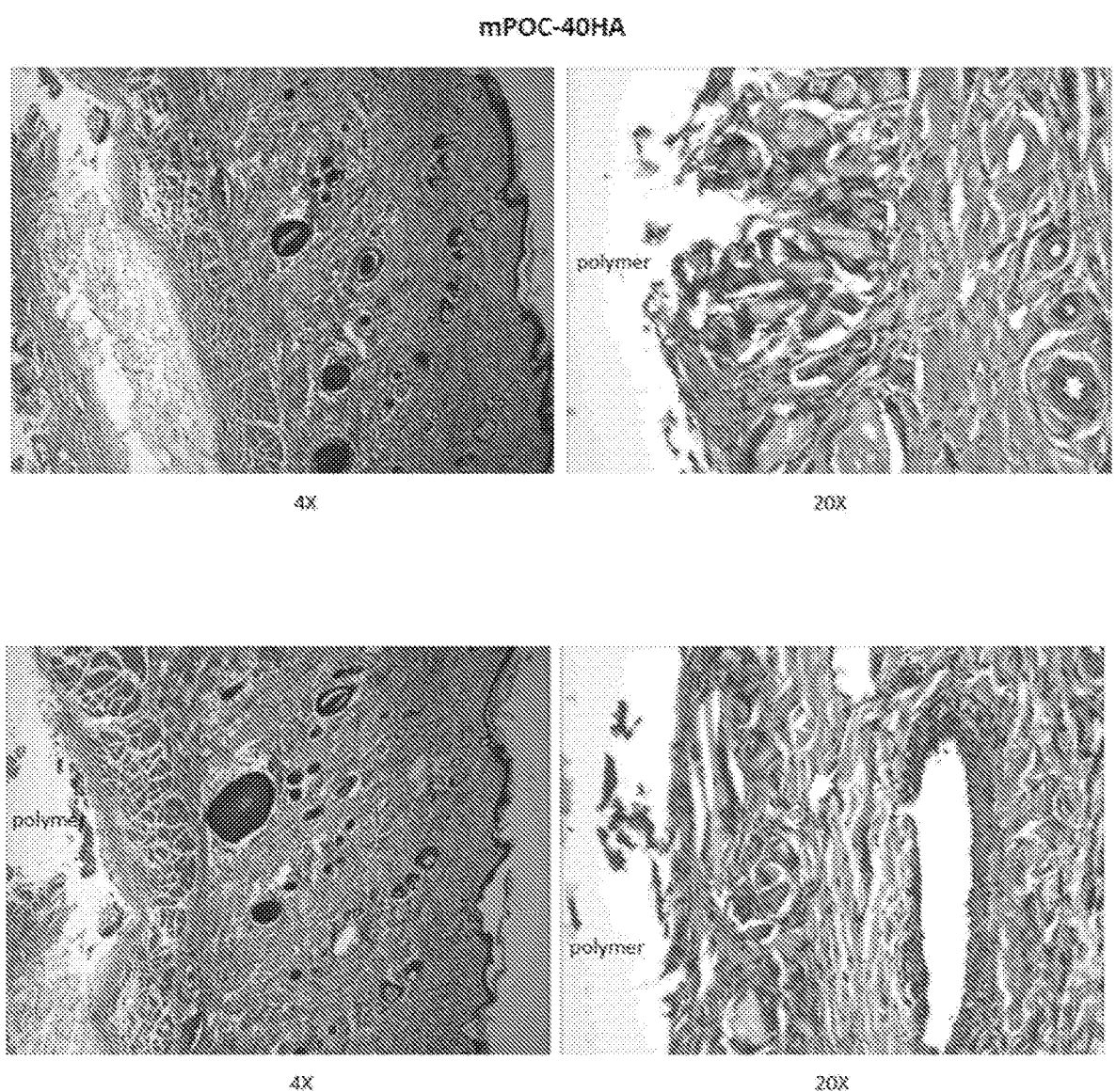
Figure 14A:
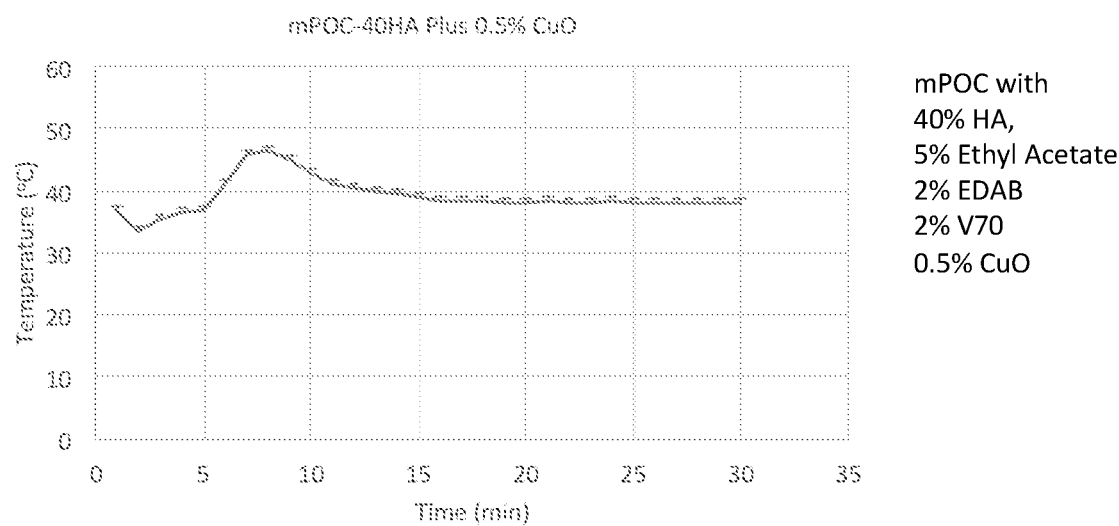
FIG. 14A-B. Graphs demonstrating that (FIG. 14A) CuO nanoparticles and (FIG. 14B) CaO are useful in accelerating curing rate of, for example, mPOC-40HA composites.
Figure 14B:
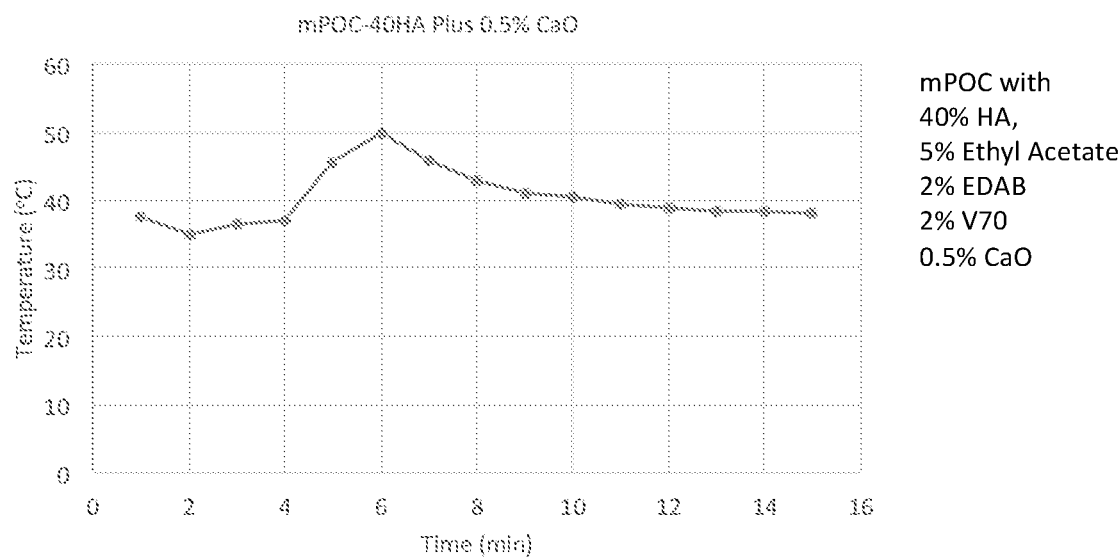

Storage mPOC-40HA premixed with V70 and stored at −20° C. overnight is still injectable and cures at 37° C. (FIG. 11).

Compression Testing

Following curing of the liquid polymer-ceramic composite at 37° C., samples were tested via compression (FIG. 12). The sample was a cylinder with 9 mm diameter and 5 mm height. The test was set to compress 1 mm. The results indicated that after 30 min, the polymer became solid. After 1 hour, polymer modulus was significantly increased.

Results

Polymer Characterization

The methacrylated polymers were characterized by $^1$H-NMR as shown in FIGS. 1(A,C). The spectrum (FIG. 1, peaks A through E-2) confirms the successful functionalization of POC and PDDC with the methacrylate group. The peaks labeled F correspond to the methylene protons from citric acid, and peaks G through J and L were assigned to protons from 1,8-dodecanediol and 1,12-dodecanediol, respectively. FTIR analysis of the poly(diol citrate) elastomers is shown in FIGS. 1(B,D). The presence of the peak at 1600 cm$^{-1}$ for mPOC and mPDC corresponds to the methacrylate alkene, confirming the successful methacrylation of POC and PDDC.

Figure 17:
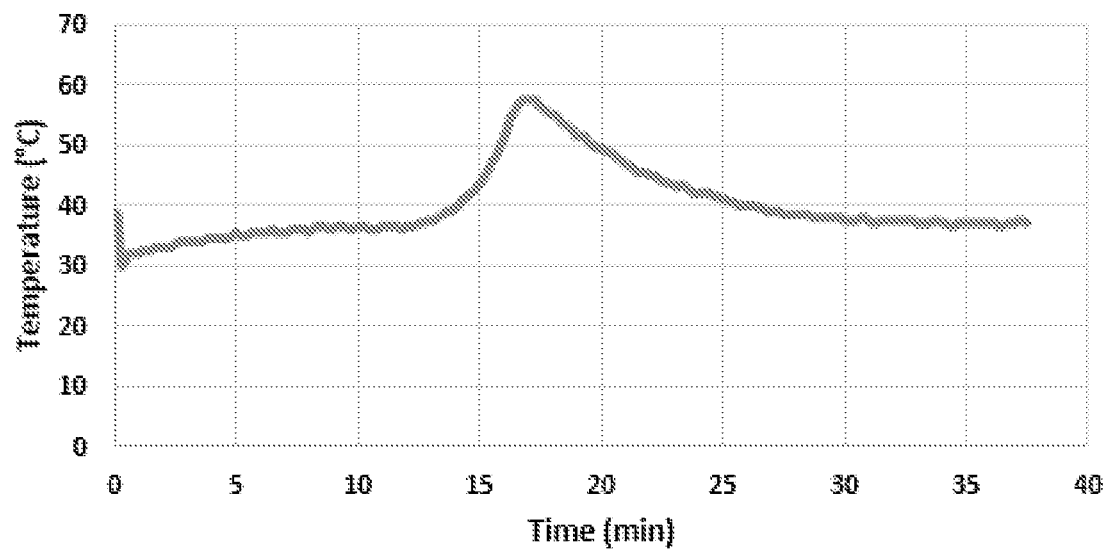
FIG. 17. Heat evolved during polymerization. Representative temperature vs. time curves for exemplary formulations: (top) mPOC-20HA and (bottom) mPOC-40HA. The data represents two independent experiments for each formulation group.
Figure 17:
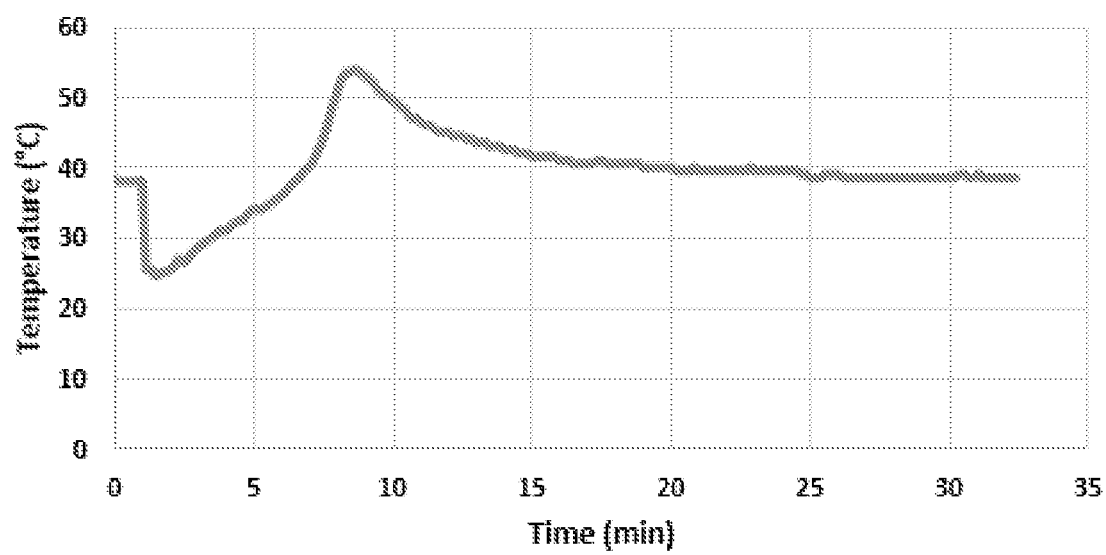

Six formulations of poly(diol citrates) were created as shown in Table 1. The weight percentages were calculated based on the total mass of the final mixture. The initiator (V70) and accelerator, ethyl 4-dimethylaminobenzoate (EDAB), amounts were optimized to yield a formulation setting time of approximately fifteen minutes. The ethyl acetate (EtOAc) weight percentage was determined to be the minimum amount required to dissolve all the components and retain injectability. Thermal properties of each formulation were characterized by measuring the heat evolved during polymerization (FIG. 17). Incorporating hydroxyapatite lowered the maximum temperature during the free radical polymerization process. The temperature recordings were obtained according to the ASTM F451 standard. Rheological assessment indicates that the addition of hydroxyapatite increases the time needed for polymerization of both poly(diol citrates) (FIG. 2A-F). The maximum temperature reached during polymerization and the total time to gel point are summarized in Table 5 for all formulations. The gel point was determined to be when the complex viscosity increased by an order of magnitude.

TABLE 5

Maximum temperature and gel point. Summary of the maximum temperature recordings and gel points for each formulation tested.

| Formulation | Maximum temperature (° C.) | Gel point (min) |
|---|---|---|
| mPOC | — | 14.3 ± 0.354 (n = 2) |
| mPOC-20HA | 52.5 (n = 2) | 14.0 ± 1.03 (n = 2) |
| mPOC-40HA | 54 (n = 1) | 16.3 ± 0.707 (n = 2) |
| mPDC | — | 15.0 (n = 1) |
| mPDC-20HA | — | 15.4 ± 0.141 (n = 2) |
| mPDC-40HA | — | 13.7 ± 0.919 (n = 2) |

Mechanical Tests

FIGS. 3A-E show that compression tests of poly(diol citrates) produced stress-strain curves for elastomeric materials. The polymer only group exhibited higher ultimate compressive strength and modulus compared to the hydroxyapatite composites, with modulus, ultimate compressive strength, and strain percentage at failure decreasing as hydroxyapatite weight percentage increases (Table 2). Compressive strength of POC composites were as high as 0.791±0.102 GPa, with ultimate compressive strengths of 220±27.6 MPa and strain at failure of 49.7±1.68%.

In Vitro Degradation Studies

Figure 4:
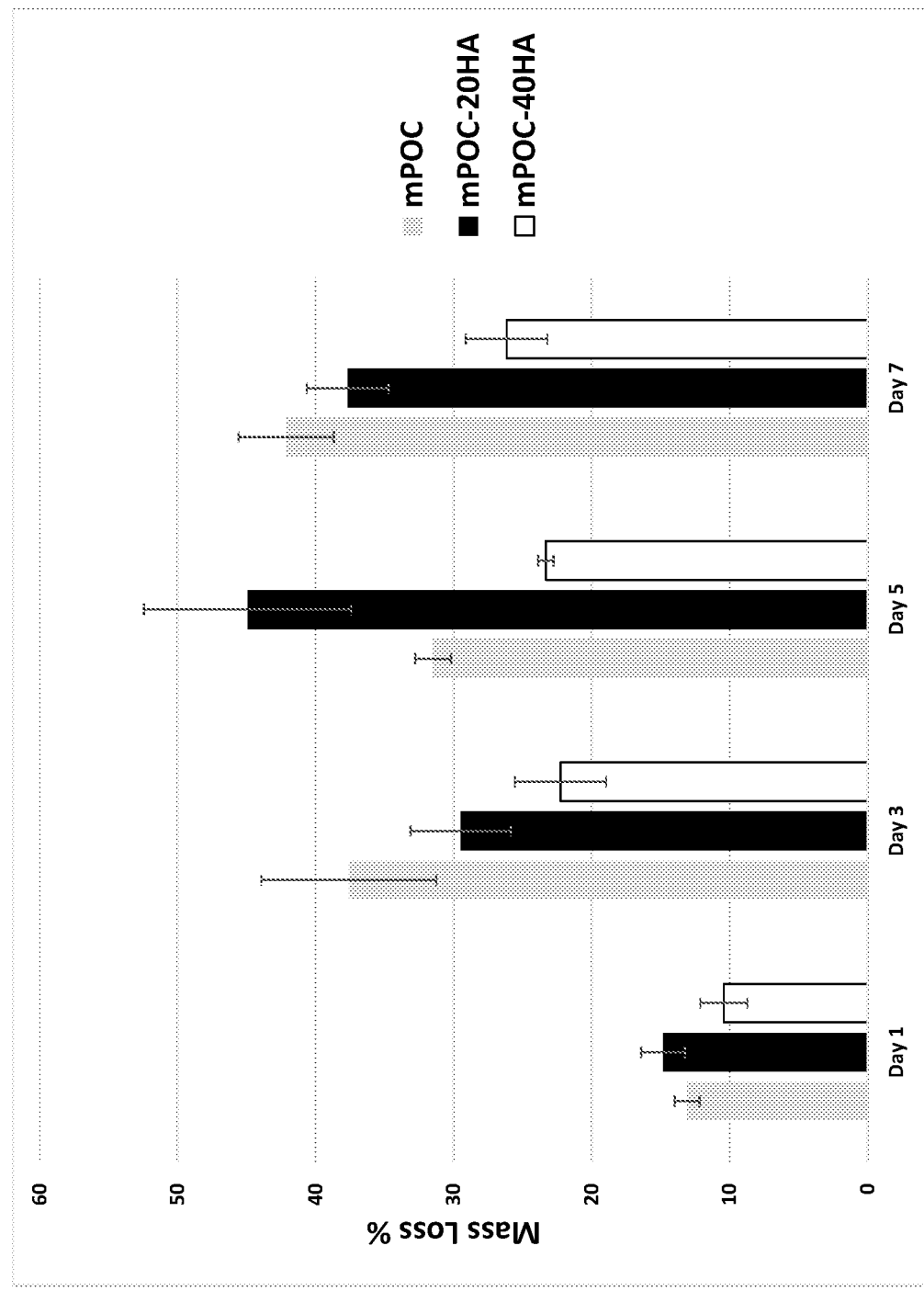
FIG. 4. Accelerated degradation of tested formulations. Cylindrical specimens were placed in a 0.5 M NaOH solution and incubated at 37° C. Composites exhibited a slower degradation rate relative to the polymer only group. The data represent five independent experiments for each time point for each formulation group. Panel FIG. 5. Scanning electron micrograph of formulation surface after accelerated degradation. Cylindrical specimens were placed in 0.5 M NaOH solution and incubated at 37° C. for 1 and 7 days. (Panel A) mPOC after 1 day. (Panel B) mPOC after 7 days. (Panel C) mPOC-20HA after 1 day. (Panel D) mPOC-20HA after 7 days. (Panel E) mPOC-40HA after 1 day. (F) mPOC-40HA after 7 days.
Figure 5:
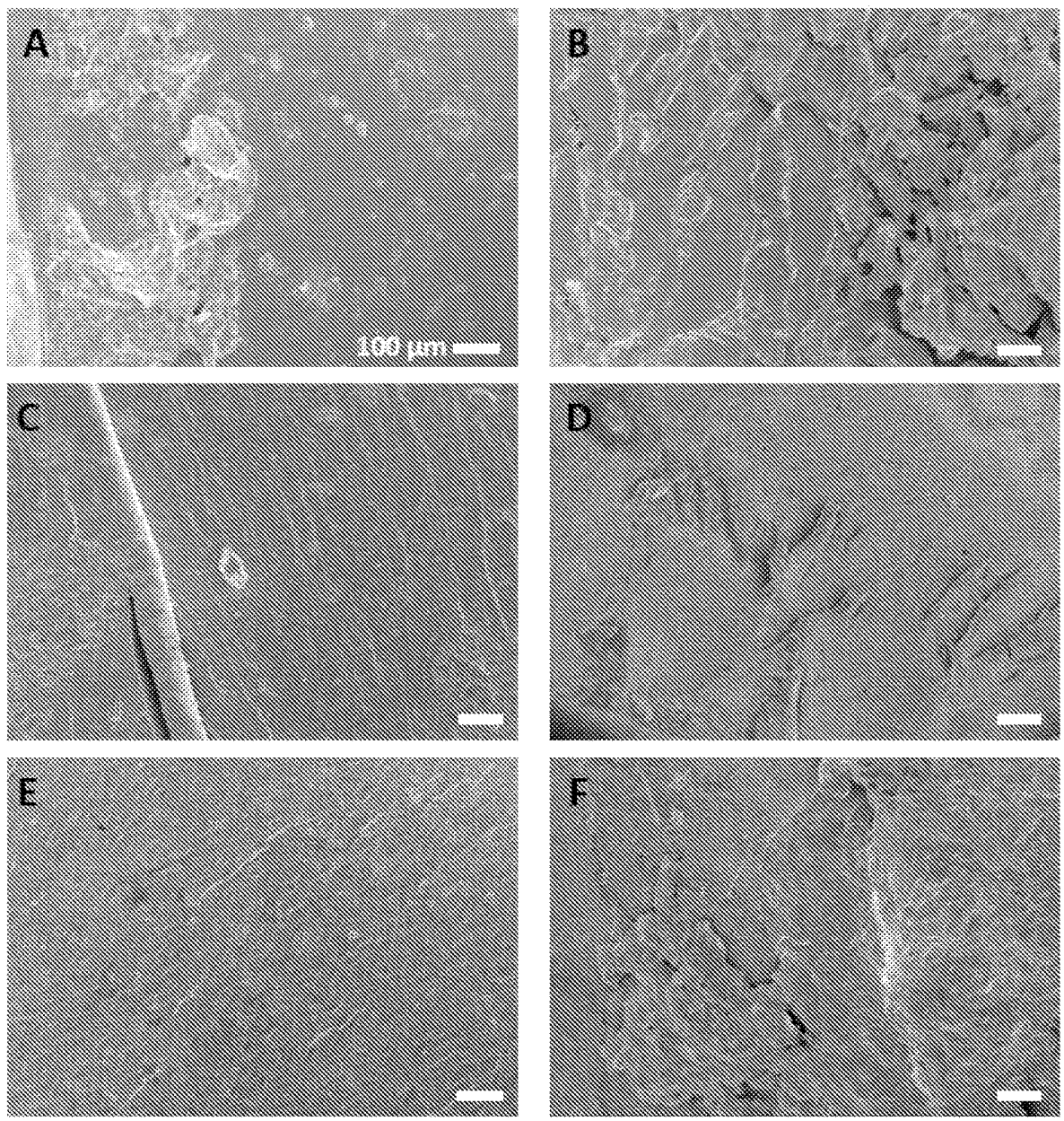

The accelerated degradation of poly(diol citrates) over a seven day period is represented in FIG. 4 and summarized in Table 4. Polymer composites containing hydroxyapatite presented slower degradation rates compared to mPOC alone, with an increase in hydroxyapatite concentration resulting in a decrease in degradation rates. SEM images of each formulations were taken at days 1 and 7 (FIG. 5). Clear surface degradation can be seen at the 7 day time point.

TABLE 4

Summary of accelerated degradation study of tested formulations

| Formulation | Mass loss % (day 1) | Mass loss % (day 7) |
|---|---|---|
| mPOC (n = 5) | 13.1 ± 0.888 | 42.1 ± 3.46 |
| mPOC-20HA (n = 5) | 14.8 ± 1.57 | 37.7 ± 2.98 |
| mPOC-40HA (n = 5) | 10.4 ± 1.70 | 26.2 ± 2.95 |

Biocompatibility Evaluation

Figure 15:
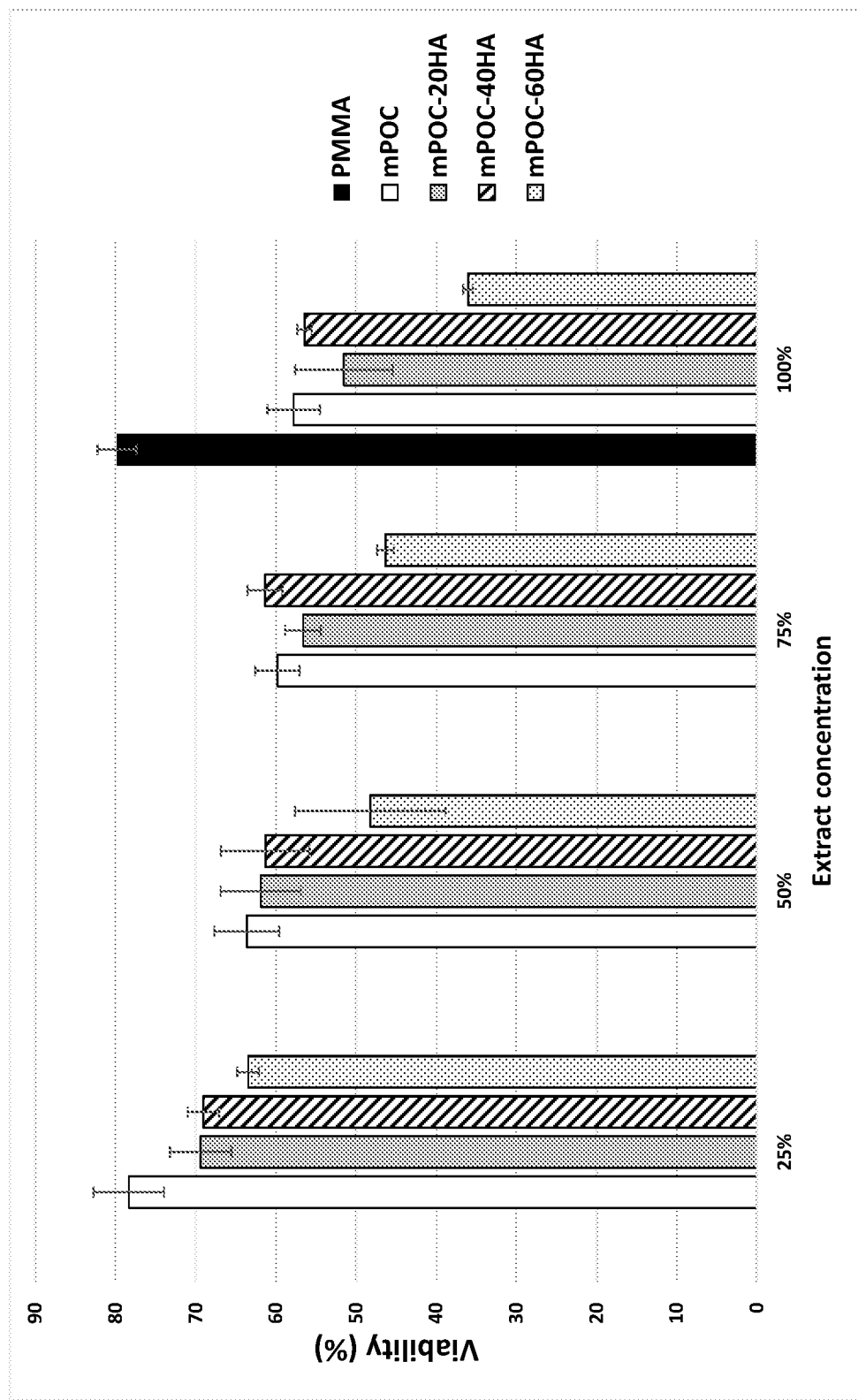
FIG. 15. In vitro cytotoxicity evaluation with MTT assay for mPOC-based formulations.

In vitro cytotoxicity was evaluated using MTT at a time point of 24 hours (FIGS. 15 and 17). Extracts were prepared from each composite and added to L929 fibroblasts. Overall, increased levels of hydroxyapatite resulted in decreased viability. Composites containing 40HA did present comparable viability results to the poly(diol citrates) alone.

Figure 6:
FIG. 6. In vivo formulation setting via subcutaneous injection in Sprague-Dawley rats. (Panel A) PMMA. (Panel B) mPOC. (Panel C) mPOC-40HA. Each injection was 100 µL and the implants were explanted after 1 hr. All of the samples were cured after 1 hr.
Figure 7:
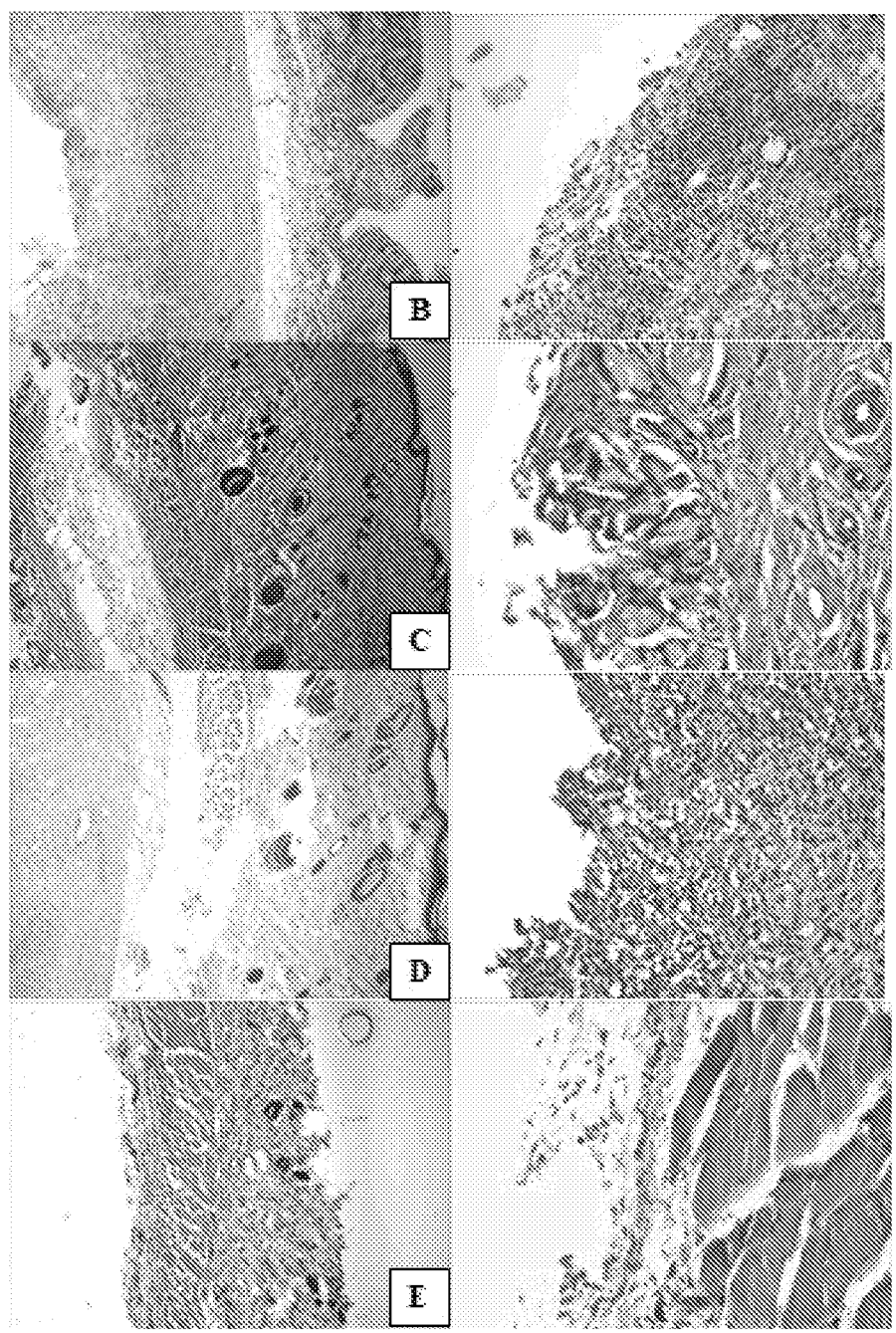
FIG. 7. Composites that solidify with body temperature are biocompatible. Hematoxylin and eosin stain of a tissue section that contained a mPOC-40HA composite that was injected subcutaneously and explanted after 1 hr of the injection. Connective tissue surrounding the implant appears normal. (Panel B) mPOC. (Panel C) mPOC-40HA. (Panel D) mPDC. (Panel E) mPDC-40HA.

In vivo cytotoxicity was evaluated via subcutaneous injections in Sprague-Dawley rats. Samples were injected into the back of the animals and explanted after 1 hour (FIG. 6). Additionally, samples were injected and explanted after 1 week to determine the foreign body response to each composite (FIG. 7). Poly(diol citrate) polymers alone produced increased acute inflammatory responses, as seen by the presence of leukocytes and macrophages within the tissue surrounding the polymers (FIGS. 7B and 7D). Fewer macrophages are seen in the 40HA composites for both mPOC and mPDC combinations, indicating that the presence of hydroxyapatite influences the natural inflammatory response (FIGS. 7C and 7E).

Discussion

The poly(diol citrate) composites observed in this study display mechanical properties, degradation rates, and biocompatible characteristics necessary for bone tissue engineering applications [Ref 1; herein incorporated by reference in its entirety]. Unlike PMMA, the poly(diol citrates) are able to degrade over time, allowing for ingrowth of natural bone into surgical defects. The ability of the composites to cure at body temperature through addition of V70 also circumvents the onset of tissue necrosis, an issue found with PMMA applications due to its high thermal heat during polymerization. Additionally, incorporation of HA nanoparticles enhances the biological response to the composites herein.

NMR (FIGS. 1A, C) of methacrylated poly(diol citrates) confirmed the presence of methyl groups and subsequent building blocks of non-methacrylated versions [Ref 11; herein incorporated by reference in its entirety]. Characteristic peaks from FTIR (FIGS. 1B, D) indicate the retention of key attributes after methacrylation. Composites of poly(diol citrates) were formulated to carry out subsequent experiments (Table 1). Heat evolved during polymerization ranged from 50-60° C., with the addition of HA decreasing the maximum temperature achieved (FIG. 17 and Table 5). This is likely due to HA absorbing additional heat during the exothermic reaction of polymerization. Addition of HA to poly(diol citrates) increased the amount of time needed for polymerization (FIG. 2A-F). Dispersion of nanoparticles within the polymer construct likely disrupts the polymer network, limiting its ability to cure at a faster rate.

Compressive strengths were found to decrease as the ratio of HA particles in composites increased (FIGS. 3A-E). Conversely, degradation rates of composites decreased as HA increased (FIG. 4). It is inferred that while the HA disrupted the composition of the polymer, directly impacting the ultimate compressive strength and strains, it allowed for slower degradation of the poly(diol citrate) construct. It is noted that there was a spike in mass loss for the mPOC-20HA composite at day 1 and 5 due to improper dispersion of HA particles throughout the construct, thus creating pockets of pure polymer that resulted in increased degradation and mass loss. Degradation over the 7-day period is qualitatively depicted in FIG. 5. At day 1, a smooth surface is found for all composites. At day 7, noticeable degradation can be seen through the formation of craters and ridges. Overall, each degradation profile is comparable indicating that the addition of HA does not affect surface degradation over time.

Figure 16:
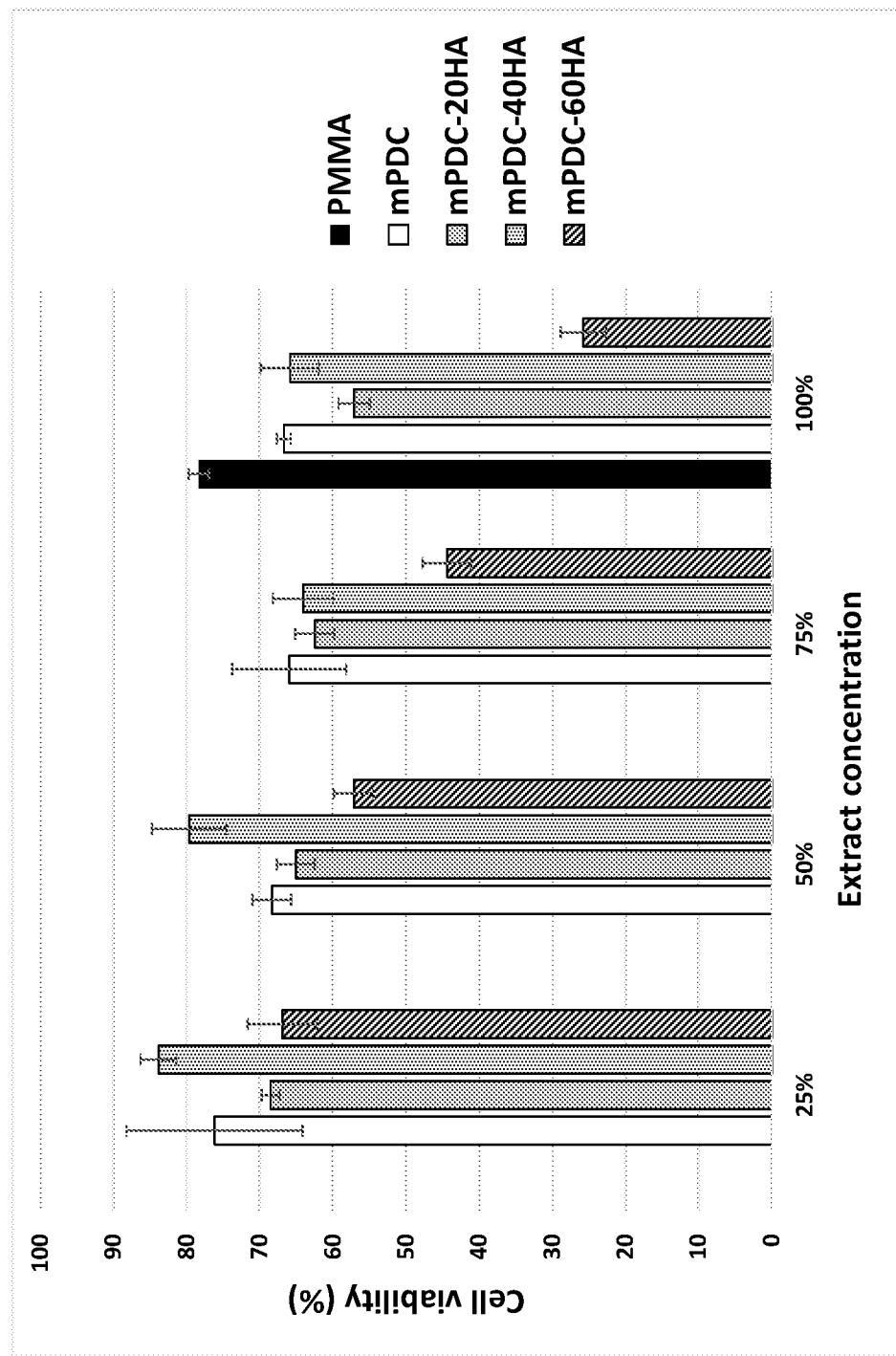
FIG. 16. In vitro cytotoxicity evaluation with MTT assay for mPDC-based formulations.

Preliminary in vitro and in vivo poly(diol citrate) results indicate their cell compatibility [Refs. 9,11; herein incorporated by reference in their entireties]. Addition of HA supported those previously reported results. FIGS. 15 and 16 present results obtained from in vitro studies in L929 fibroblastic cells. Increased amounts of HA resulted in decreased cell viability over the 24-hour period. Cell viability compared between groups of increasing extract concentration remain consistent, indicating that the pure polymers will not be toxic at low and high concentrations. Overall, the 40HA groups fared best compared to the other composites, yet still does not produce a cell compatibility reading as high as PMMA. In in vitro culture, PMMA is cured before introduction to cells, circumventing the issue of high polymerization heat that could cause cell death and subsequent tissue necrosis. Given the inertness and nondegradable nature of PMMA, the high cell viability is expected when compared to the degradable poly(diol citrates).

To determine the curing time and biocompatibility of composites, subcutaneous injections were administered in the backs of Sprague Dawley rats. To verify curing time, composites were injected and explanted at 1 hour (FIG. 6). Each group cured within the hour, with some spreading of PMMA and poly(diol citrates) occurring around the area of injection. The HA composites spread minimally, and resulted in a semi-spherical construct. It is also noted that the HA composites are more opaque than PMMA and poly(diol citrates), indicating the presence and dispersion of HA throughout the construct. Subcutaneous injections were also applied and extracted after 1 week to observe the inflammatory response to each composite (FIG. 7). Acute inflammatory responses were observed for all composites at 1 week, which is consistent with injection of a foreign material into the body. Increased response to the poly(diol citrates) is apparent (FIGS. 7B, D) as can be seen by the large presence of inflammatory cells, which includes macrophages. FIGS. 7C and 7E which contain HA present a decreased inflammatory response, likely due to the biocompatibility of HA.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by number, are herein incorporated by reference in their entireties.

[1] Amini, A., Laurensin, C., Nukavarapu, S. Bone Tissue Engineering: Recent Advances and Challenges. Cret Rev Biomed Eng. 2012; 40(5):363-408.

[2] Kuhn K-D. Properties of bone cement: what is bone cement. In: Breusch S, Malchau H, eds. The well cemented total hip arthroplasty. Heidelberg: Springer Medizin Verlag, 2005:52-9.

[3] Webb, J. C. J., Spencer, R. F. The role of polymethylmethacrylate bone cement in modern orthopaedic surgery. J Bone Joint Surg. 2007; 89-B:851-7.

[4] Peter, S. J., Miller, S. T., Zhu, G., Yasko, A. W., Mikos, A. G. In vivo degradation of poly(propylene fumarate)/beta-tricalcium phosphate injectable composite scaffold. J Biomed Mater Res. 1998; 41:1-7.

[5] Rezwan, K., Chen, Q. Z., Blaker, J. J., Boccaccini, A. R. Biodegradable and bioactive porous polymer/inorganic composite scaffolds for bone tissue engineering. Biomaterials. 2006 June; 27(18):3413-31.

[6] Morgan, E. F., Yetkinler, D. N., Constantz, B. R., Dauskardt, R. H. Mechanical properties of carbonated apatite bone mineral substitute: strength, fracture, and fatigue behavior. J. Mater. Sci. Mater. Med. 1997; 8:559-570.

[7] Daldy, M. J., Di Silvio, L., Harper, E. J., Bonfield, W. Increasing hydroxyapatite incorporation into poly(methyl methacrylate) cement increases osteoblast adhesion and response. Biomaterials. 2002; 23(2):569-576.

[8] Stephenson, P. K., Freeman, M. A., Revell, P. A., Germain, J., Tuke, M., Pirie, C. J. The effect of hydroxyapatite coating on ingrowth of bone into cavities of an implant. J Arthroplasty. 1991; 6:51-58.

[9] Yang, J., Webb, A. R., Ameer, G. A. Novel citric acid-based biodegradable elastomers for tissue engineering. Adv Mater 2004; 16:511-6.

[10] Webb, A. R., Yang, J., Ameer, G. A. Biodegradable polyester elastomers in tissue engineering. Expert Opin Biol Ther 2004; 4:801-12.

[11] Yang, J., Webb, A. R., Pickerill, S., Hageman, G., Ameer, G. Synthesis and evaluation of poly(diol citrate) biodegradable elastomers. Biomaterials. 27 (2006):1889-1898.

[12] Chia, L. H. L., Jacob, J., Boey, F. Y. C. Radiation curing of poly-methyl-methacrylate using a variable power microwave source. J Mater Processing Tech. 1995; 48(1-4):445-449.

[13] Peniche, C., Arguelles-Monal, W., Davidenko, N., Sastre, R., Gallardo, A., San Roman, J. Self-curing membranes of chitosan/PAA IPNs obtained by radical polymerization: preparation, characterization, and interpolymer complexation. Biomaterials. 1999; 20(10):1869-1878.

[14] Dae Han, C., Lee, D. S. Analysis of the curing behavior of unsaturated polyester resins using the approach of free radical polymerization. J Appl. Polym. Sci. 1987; 33:2859-2876. Doi:10.1003/app.1987.070330820.

[15] Chien, H., Xu, X., Ella-Menye, J., Tsai, W., Jiang, S. High viability of cells encapsulated in degradable poly (carboxybetaine) hydrogels. Langmuir. 2012; 28(51): 17778-17784.

[16] Gosain, A. K., Song, L. Riordan, P., Amarante, M. T., Nagy, P. G., Wilson, C. R. et al. A 1-year study of os-teoinduction in hydroxyapatite-derived biomaterials in an adult sheep model: part I. Plast Reconstr Surg. 2002; 109(2):619-630.

[17] Hasegawa, S., Neo, M., Tamura, J., Fujibayashi, S., Takemoto, M., Shikinami, Y., Okazaki, K., Nakamura, T. In vivo evaluation of a porous hydroxyapatite/poly-DL-lactide composite for bone tissue engineering. J Biomed Mater Res A. 2007; 81(4):930-938.

[18] Higashi, S., Yamamuro, T., Nakamura, T., Ikada, Y., Hyon, S. H., Jamshidi, K. Polymer-hydroxyapatite composites for biodegradable bone fillers. Biomaterials. 1986; 7(3):183-187.

The invention claimed is:

1. A composite material comprising:
(a) an acrylated or methacrylated poly(diol citrate) polymer, wherein the acrylated or methacrylated poly(diol citrate) polymer comprises the formula:

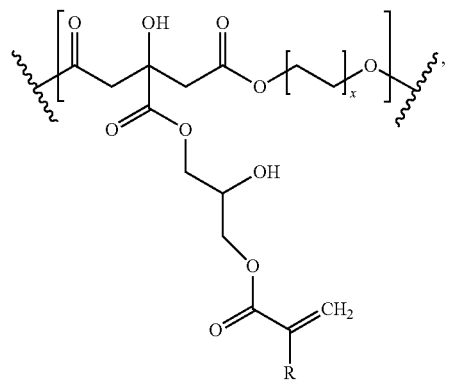

wherein R is H or $CH_3$; wherein x is 1-16;
(b) a thermoresponsive initiator compound, wherein an increase in temperature above a threshold temperature results in radical formation from the thermoresponsive initiator compound, and the radical formation initiates curing of the acrylated or methacrylated poly(diol citrate) polymer into a cured polymer; and
(c) a bioceramic component.

2. The composite material of claim 1, wherein the bioceramic component is at least 10 wt % of the composite material.

3. The composite material of claim 1, wherein the bioceramic component comprises hydroxyapatite (HA) and/or β-tricalcium phosphate (β-TCP).

4. The composite material of claim 1, wherein the acrylated or methacrylated polymer is a liquid and/or is soluble in water and/or organic solvent.

5. The composite material of claim 1, wherein x is 8, 10, or 12.

6. The composite material of claim 1, wherein at least 10% of the citric acid monomers of the acrylated or methacrylated poly(diol citrate) polymer display a methacrylate or acrylate.

7. The composite material of claim 6, wherein at least 90% of the citric acid monomers of the acrylated or methacrylated poly(diol citrate) polymer display a methacrylate or acrylate.

8. The composite material of claim 1, wherein the thermoresponsive initiator compound is a diazo compound.

9. A composition comprising a cured composite material prepared by thermally-induced curing of the composite material of claim 1.

10. The composition of claim 9, wherein thermally-induced curing occurs at a temperature between 32 and 43° C.

11. A method comprising administering the composite material of claim 1 to a bone defect or fracture and allowing the composite material to cure.

* * * * *